(12) United States Patent
Kleen et al.

(10) Patent No.: US 7,169,193 B2
(45) Date of Patent: Jan. 30, 2007

(54) USE OF SUGAR SURFACTANTS AND FATTY ACID PARTIAL GLYCERIDES

(75) Inventors: Astrid Kleen, Erkrath (DE); Horst Hoeffkes, Duesseldorf (DE); Christa Rohland, Duesseldorf (DE); Bianca Frauendorf, Velbert (DE)

(73) Assignee: Henkel Kommanditgesellschaft Auf Aktien (Henkel KGAA), Duesseldorf (DE)

( * ) Notice: Subject to any disclaimer, the term of this patent is extended or adjusted under 35 U.S.C. 154(b) by 0 days.

(21) Appl. No.: 10/281,578

(22) Filed: Oct. 28, 2002

(65) Prior Publication Data

US 2003/0150069 A1 Aug. 14, 2003

Related U.S. Application Data

(63) Continuation of application No. PCT/EP01/04375, filed on Apr. 18, 2001.

(30) Foreign Application Priority Data

Apr. 28, 2000 (DE) ................. 100 20 887

(51) Int. Cl.
*A61Q 5/10* (2006.01)
(52) U.S. Cl. .................. 8/405; 8/406; 8/435; 8/907
(58) Field of Classification Search .............. 8/406, 8/435, 907, 405
See application file for complete search history.

(56) References Cited

U.S. PATENT DOCUMENTS

| | | | |
|---|---|---|---|
| 1,985,424 A | 12/1934 | Piggott | |
| 2,016,962 A | 10/1935 | Flint et al. | |
| 2,703,798 A | 3/1955 | Schwartz | |
| 4,237,253 A | 12/1980 | Jacquet et al. | |
| 4,393,886 A | 7/1983 | Strasilla et al. | |
| 4,814,101 A | 3/1989 | Schieferstein et al. | |
| 4,865,774 A | 9/1989 | Fabry et al. | |
| 4,931,218 A | 6/1990 | Schenker et al. | |
| 5,294,726 A | 3/1994 | Behler et al. | |
| 5,312,932 A | 5/1994 | Behler et al. | |
| 5,322,957 A | 6/1994 | Fabry et al. | |
| 5,484,531 A | 1/1996 | Kuehne et al. | |
| 5,716,418 A | 2/1998 | Matzik et al. | |
| 5,773,595 A | 6/1998 | Weuthen et al. | |
| 6,033,652 A | 3/2000 | Ansmann | |
| 6,740,130 B2 * | 5/2004 | Sander et al. ............ | 8/405 |

FOREIGN PATENT DOCUMENTS

| | | |
|---|---|---|
| CA | 2 066 226 | 3/1991 |
| DE | 28 17 369 A1 | 10/1978 |
| DE | 37 23 354 A1 | 1/1989 |
| DE | 37 25 030 A1 | 2/1989 |
| DE | 39 26 344 A1 | 2/1991 |
| DE | 39 29 973 A1 | 3/1991 |
| DE | 42 04 700 A1 | 8/1993 |
| DE | 0 561 825 B1 | 9/1995 |
| DE | 44 13 686 A1 | 10/1995 |
| DE | 196 19 645 A1 | 11/1997 |
| DE | 197 38 866 A1 | 3/1999 |
| DE | 198 05 703 A1 | 8/1999 |
| DE | 199 07 714 A1 | 8/2000 |
| DE | 199 19 089 A1 | 11/2000 |
| DE | 199 26 526 A1 | 12/2000 |
| EP | 0 047 714 B1 | 10/1985 |
| EP | 0 217 274 A2 | 4/1987 |
| EP | 0 283 817 B1 | 12/1990 |
| EP | 0 530 229 B1 | 6/1995 |
| EP | 0 561 999 B1 | 1/1996 |
| EP | 0 711 542 A1 | 5/1996 |
| EP | 0 655 905 B1 | 10/1996 |
| GB | 2 104 091 A | 3/1983 |
| WO | WO 92/06984 A1 | 4/1992 |
| WO | WO 92/13829 A1 | 8/1992 |

OTHER PUBLICATIONS

Anon.:"Hair Treatment agent with improved luster effect", Research Disclosure, No. 40530, Jan. 10, 1989 p. 26, XP000772356.
B. Salka,"Alkyl Polyglycosides", Cosmetics and Toiletries, vol. 108, pp. 89-94, (1993).
Biermann et al., "Alkylpolygluocoside-Technologie und Eigenschaften", Starch/Starke, vol. 45, pp. 281-288 (1993).
J. Kahre et al., "Alkylpolyglycoside-Ein neues Konzept fur Pflege und Vertraglich-keit in der Kosmetic", SOFW-Journal vol. 121, pp. 598-611 (1995).
H. Kelkenberg, "Detergenzien auf Zuckerbasis", Tenside Surfactants Detergents, vol. 25, pp. 8-13 (1988).
International Cosmetic Ingredient Dictionary and Handbook, 7th Edition (1997).
A.K. Biswas et al., "Surface-Active Properties of Sodium Salts of Sulfated Fatty Acid Monoglycerides", Journal of the American Oil Chemists Society, vol. 37, pp. 171-175 (1960).
F. U. Ahmed, "Efficient synthesis of Fatty Monoglyceride Sulfates from Fatty Acids and Fatty Acid Methyl Esters", Journal of the American Oil Chemists Society, vol. 67, pp. 8-14 (1990).
Falbe et al., Rompp-Lexikon Chemis, vol. 10, Georg thieme Verlag Stuttgart, New York, pp. 1764 (1997).
Schrader, Grundlagen und Rezepturen der Kosmetika, vol. 2, Huthig Buch Vergla Heidelberg, (1989).
Charles Zviak, "Hair Coloring", The Science of Hair Care, Chapter 7, vol. 7, Dermatology, Marcel Dekker Inc., pp. 248-250 (1986).
Charles Zviak,"Oxidation Coloring", The Science of Hair Care, Chapter 8, vol. 7, Dermatology, Marcel Dekker Inc., pp. 264-267 (1986).

* cited by examiner

*Primary Examiner*—Elli Peselev
(74) *Attorney, Agent, or Firm*—Woodcock Washburn LLP

(57) ABSTRACT

There are provided compositions for improving the wash-fastness and color intensity of colored fibers, especially keratin fibers, which comprise
a) at least one sugar surfactant chosen from the group consisting of alkyl and alkenyl oligoglycosides or fatty acid N-alkylpolyhydroxyalkylamides and
b) at least one fatty acid partial glyceride.

20 Claims, No Drawings

USE OF SUGAR SURFACTANTS AND FATTY ACID PARTIAL GLYCERIDES

CROSS REFERENCE TO RELATED APPLICATIONS

This application is a continuation under 35 U.S.C.§ 365 (c) and §120 of International Application No. PCT/EP01/04375 filed Apr. 18, 2001 and under § 119 of German Patent Application No. 100 20 887.8 filed Apr. 28, 2000.

SUMMARY OF THE INVENTION

The invention relates to the use of an active ingredient combination of sugar surfactants and fatty acid partial glycerides for color intensification and improvement of the washfastness of colorations of keratin fibers, to corresponding preparations, and to methods for coloring fibers.

BACKGROUND OF THE INVENTION

Human hair is nowadays treated in diverse ways with hair-cosmetic preparations. This includes, for example, the cleaning of the hair with shampoos, the care and regeneration with rinses and treatments, and also the bleaching, coloring and shaping of the hair using colorants, tints, waving compositions and styling preparations. In this connection, compositions for changing or nuancing the color of the head of hair play a prominent role. Disregarding the bleaching compositions which bring about an oxidative lightening of the hair as a result of degradation of the natural hair dyes, then essentially three types of hair colorants are of importance in the field of hair coloring:

For permanent, intensive colorations with corresponding fastness properties, so-called oxidation colorants are used. Such colorants usually comprise oxidation dye precursors, so-called developer components and coupler components. The developer components form the actual dyes under the influence of oxidizing agents or of atmospheric oxygen with one another or with coupling with one or more coupler components. Although the oxidation colorants are characterized by excellent, long-lasting coloring results, for colorations which look natural, it is usually necessary to use a mixture of a relatively large number of oxidation dye precursors; in many cases, direct dyes are also used for the nuancing. If the dyes formed during the course of the color development or used directly have considerably different fastnesses (e.g. UV stability, perspiration fastness, washfastness etc.), then over time a noticeable and therefore undesired color shift may result.

This phenomenon arises to a greater extent if the hair style has hair or zones of hair with differing degrees of damage. One example of this is long hair in which the tips of the hair, subjected for a long time to all possible environmental influences are usually damaged to a markedly greater degree than the relatively freshly grown zones of hair.

For temporary colorations, colorants or tints are usually used which comprise so-called substantives as coloring component. These are dye molecules which attach directly to the hair and require no oxidative process for developing the color. These dyes include, for example, henna which has already been known for a long time for coloring bodies and hair. These colorations are generally considerably more sensitive to shampooing than the oxidative colorations, meaning that an often undesired nuance shift or even a visible "decoloration" arises very much more quickly.

Finally, a new type of coloring method has recently received great attention. In this method, precursors of the natural hair dye melanin are applied to the hair; then, in the course of oxidative processes within the hair, these form nature-analogous dyes. One such method with 5,6-dihydroxyindoline as dye precursor has been described in EP-B1-530 229. In the case of use, in particular repeated use, of compositions containing 5,6-dihydroxyindoline, it is possible to restore the natural hair color in people with gray hair. The development of color can take place here with atmospheric oxygen as the sole oxidizing agent, meaning that recourse does not have to be made to any other oxidizing agent. For people with originally mid-blonde to brown hair, the indoline may be used as the sole dye precursor. For use for people with originally red and, in particular, darker to black hair color, by contrast, satisfactory results can often only be achieved through the co-use of further dye components, in particular special oxidative dye precursors. Here too, problems with regard to fastness of the colorations can arise.

There has been no lack of attempts to improve the fastness of colorations of keratin fibers. One development direction is the optimization of the dyes themselves or the synthesis of new, modified dye molecules. A further development direction is the search for additives for the colorants in order to increase the fastness of the colorations. A known solution to the problem is to add UV filters to the colorant. These filter substances are applied to the hair in the coloring process together with the dye, as a result of which, in many cases, a significant increase in the stability of the coloration toward the action of daylight or artificial light is achieved.

EP 0 655 905 B1 discloses the use of alkyl glycosides in colorants. DE-A 199 190 89 describes hair-coloring preparations containing sugar surfactants and fatty acid partial glycerides which strengthen the hair structure and are readily dermatologically compatible. However, no information with regard to color intensification and with regard to washfastness is disclosed.

Surprisingly, it has now been found that the use of the active ingredient combination according to the invention consisting of sugar surfactants and fatty acid partial glycerides, it is possible to significantly increase the washfastness and the color intensification of colorings, in particular of keratin fibers. For the purposes of the invention, washfastness is understood as meaning the retention of the original coloration with regard to nuance and/or intensity when the keratin fiber is subjected to the repeated influence of aqueous compositions, in particular surfactant-containing compositions such as shampoos. For the purposes of the invention, color intensification is understood as meaning that the coloration significantly increases in color strength as a result of application of the active ingredient combination according to the invention.

DESCRIPTION OF THE INVENTION

The present invention therefore firstly provides for the use of an active ingredient combination of a) at least one sugar surfactant (A) chosen from the group consisting of alkyl and alkenyl oligoglycosides (A1) and fatty acid N-alkylpolyhydroxyalkylamides (A2), and b) at least one fatty acid partial glyceride (B) for improving the washfastness of colorations of fibers, in particular of keratin fibers, and for increasing the color intensity.

The active ingredient combination used according to the invention improves the washfastness of colorations on artificial fibers, such as polyesters, and natural fibers, such as cotton and, in particular, keratin fibers.

Keratin fibers are understood according to the invention as meaning furs, wool, feathers and, in particular, human hair.

The active ingredient combination according to the invention comprises a sugar surfactant (A) as the first obligatory component.

According to a first embodiment (A1), the sugar surfactant is an alkyl or alkenyl oligoglycoside. These sugar surfactants represent known nonionic surfactants according to formula (I),

 (I)

in which $R^1$ is an alkyl or alkenyl radical having 4 to 22 carbon atoms, G is a sugar radical having 5 or 6 carbon atoms and p is numbers from 1 to 10. They can be obtained by the relevant methods of preparative organic chemistry. By way of representation of the extensive literature, reference may be made here to the review article by Biermann et al. in Starch 45, 281 (1993), B. Salka in Cosm. Toil. 108, 89 (1993) and J. Kahre et al. in SÖFW Journal Issue 8, 598 (1995).

The alkyl and alkenyl oligoglycosides can be derived from aldoses or ketoses having 5 or 6 carbon atoms, preferably from glucose. The preferred alkyl and/or alkenyl oligoglycosides are thus alkyl and/or alkenyl oligoglucosides. The index number p in the general formula (I) gives the degree of oligomerization (DP), i.e. the distribution of mono- and oligoglycosides and is a number between 1 and 10.

While p in the individual molecule must always be an integer and here primarily can assume the values p=1 to 6, the value p for a certain alkyl oligoglycoside is an analytically determined parameter which is in most cases a fraction. Preference is given to using alkyl and/or alkenyl oligoglycosides with an average degree of oligomerization p of from 1.1 to 3.0. From a performance point of view, preference is given to those alkyl and/or alkenyl oligoglycosides whose degree of oligomerization is less than 1.7 and is in particular between 1.2 and 1.4. The alkyl or alkenyl radical $R^1$ can be derived from primary alcohols having 4 to 11, preferably 8 to 10, carbon atoms. Typical examples are butanol, caproic alcohol, caprylic alcohol, capric alcohol and undecyl alcohol, and technical-grade mixtures thereof, as are obtained, for example, during the hydrogenation of technical-grade fatty acid methyl esters or in the course of the hydrogenation of aldehydes from the Roelen oxo synthesis. Preference is given to alkyl oligoglucosides of chain length $C_8$–$C_{10}$ (DP=1 to 3), which are formed as forerunner in the distillative separation of technical-grade $C_8$–$C_{18}$-coconut fatty alcohol and may be contaminated with a fraction of less than 6% by weight of $C_{12}$-alcohol, and also alkyl oligoglucosides based on technical-grade $C_{9/11}$-oxo alcohols (DP=1 to 3). The alkyl or alkenyl radical $R^1$ can also be derived from primary alcohols having 12 to 22, preferably 12 to 14, carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, and technical-grade mixtures thereof, which can be obtained as described above. Preference is given to alkyl oligoglucosides based on hydrogenated $C_{12/14}$-cocoalcohol with a DP of from 1 to 3.

According to a second embodiment (A2) of the invention, the sugar surfactant is a fatty acid N-alkylpoly-hydroxyalkylamide, a nonionic surfactant of the formula (II),

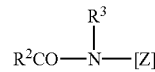 (II)

in which $R^2CO$ is an aliphatic acyl radical having 6 to 22 carbon atoms, $R^3$ is hydrogen, an alkyl or hydroxyalkyl radical having 1 to 4 carbon atoms and [Z] is a linear or branched polyhydroxyalkyl radical having 3 to 12 carbon atoms and 3 to 10 hydroxyl groups.

The fatty acid N-alkylpolyhydroxyalkylamides are known substances which can usually be obtained by reductive amination of a reducing sugar with ammonia, an alkylamine or an alkanolamine and subsequent acylation with a fatty acid, a fatty acid alkyl ester or a fatty acid chloride. With regard to the method for their preparation, reference may be made to the U.S. patent specifications U.S. Pat. No. 1,985,424, U.S. Pat. No. 2,016,962 and U.S. Pat. No. 2,703,798, and the international patent application WO 92/06984. An overview on this topic by H. Kelkenberg is given in Tens. Surf. Det. 25, 8 (1988). The fatty acid N-alkylpolyhydroxyalkylamides are preferably derived from reducing sugars having 5 or 6 carbon atoms, in particular from glucose. The preferred fatty acid N-alkylpolyhydroxyalkylamides therefore represent fatty acid N-alkylglucamides, as are given by the formula (III):

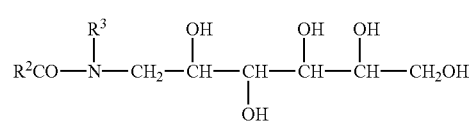 (III)

As fatty acid N-alkylpolyhydroxyalkylamides, preference is given to using glucamides of the formula (III) in which $R^3$ is hydrogen or an alkyl group and $R^2CO$ is the acyl radical of caproic acid, caprylic acid, capric acid, lauric acid, myristic acid, palmitic acid, palmoleic acid, stearic acid, isostearic acid, oleic acid, elaidic acid, petroselic acid, linoleic acid, linolenic acid, arachidic acid, gadoleic acid, behenic acid or erucic acid or technical-grade mixtures thereof. Particular preference is given to fatty acid N-alkylglucamides of the formula (III) which are obtained by reductive amination of glucose with methylamine and subsequent acylation with lauric acid or $C_{12/14}$-coconut fatty acid or a corresponding derivative. The polyhydroxyalkylamides can also be derived from maltose and palatinose.

The sugar surfactant is present in the compositions used according to the invention preferably in amounts of 0.1–20% by weight, based on the total composition. Amounts of 0.5–5% by weight are particularly preferred.

The second obligatory component of the active ingredient combination according to the invention are fatty acid partial glycerides. These fatty acid partial glycerides are monoglycerides, diglycerides and technical-grade mixtures thereof. When using technical-grade products, it is also possible for small amounts of triglycerides to be present as a result of the preparation. The partial glycerides preferably conform to the formula (IV), $$\begin{aligned}&CH_2O(CH_2CH_2O)_mR^4\\&|\\&CHO(CH_2CH_2O)_nR^5\quad\quad\quad\quad\quad\quad\quad\quad\quad\text{(IV)}\\&|\\&CH_2O(CH_2CH_2O)_qR^6\end{aligned}$$

in which $R^4$, $R^5$ and $R^6$, independently of one another, are hydrogen or a linear or branched, saturated and/or unsaturated acyl radical having 6 to 22, preferably 12 to 18, carbon atoms, with the proviso that at least one of these groups is an acyl radical and at least one of these groups is hydrogen. The sum (m+n+q) is 0 or numbers from 1 to 100, preferably 0 or 5 to 25. Preferably, $R^4$ is an acyl radical and $R^5$ and $R^6$ are hydrogen and the sum (m+n+q) is 0. Typical examples are mono- and/or diglycerides based on caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, elaeostearic acid, arachidic acid, gadoleic acid, behenic acid and erucic acid, and technical-grade mixtures thereof. Preference is given to using oleic acid monoglycerides.

The fatty acid partial glyceride is present in the compositions used according to the invention preferably in amounts of 0.1–20% by weight, in particular 0.5–5% by weight, based on the total composition.

The teaching according to the invention also includes embodiments in which the active ingredient combination comprises two or more sugar surfactants and/or two or more fatty acid partial glycerides.

Further advantageously it has been found that polymers can aid the color-retaining action of the active ingredient complex according to the invention. In a preferred embodiment, polymers are therefore added to the compositions used according to the invention, with cationic, anionic and amphoteric polymers having proven particularly effective.

Cationic polymers are understood as meaning polymers which have, in the main chain and/or side chain, a group which may be "temporarily" or "permanently" cationic. According to the invention, "permanently cationic" is used to refer to those polymers which have a cationic group irrespective of the pH of the composition. These are usually polymers which contain a quaternary nitrogen atom, for example in the form of an ammonium group. Preferred cationic groups are quaternary ammonium groups. In particular, those polymers in which the quaternary ammonium group are bonded via a $C_{1-4}$-hydrocarbon group to a polymer main chain constructed from acrylic acid, methacrylic acid or derivatives thereof have proven particularly suitable.

Homopolymers of the general formula (V),

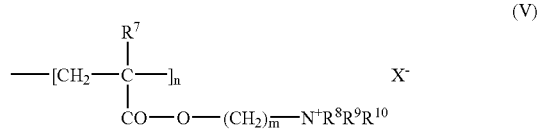
(V)

in which $R^7$=—H or —$CH_3$, $R^8$, $R^9$ and $R^{10}$, independently of one another, are chosen from $C_{1-4}$-alkyl, -alkenyl or hydroxyalkyl groups, m=1, 2, 3 or 4, n is a natural number and $X^-$ is a physiologically compatible organic or inorganic anion, and also copolymers consisting essentially of the monomer units listed in formula (V) and also nonionogenic monomer units are particularly preferred cationic polymers. Within the scope of these polymers, preference is given according to the invention to those for which at least one of the following conditions applies:

$R^7$ is a methyl group
$R^8$, $R^9$ and $R^{10}$ are methyl groups
m has the value 2.

Suitable as physiologically compatible counterions $X^-$ are, for example, halide ions, sulfate ions, phosphate ions, methosulfate ions, and organic ions, such as lactate, citrate, tartrate and acetate ions. Preference is given to halide ions, in particular chloride.

A particularly suitable homopolymer is the, if desired crosslinked, poly(methacryloyloxyethyltrimethylammonium chloride) with the INCI name Polyquaternium-37. The crosslinking can if desired take place using polyolefinically unsaturated compounds, for example divinylbenzene, tetraallyloxyethane, methylenebisacrylamide, diallyl ether, polyallyl polyglyceryl ether, or allyl ethers of sugars or sugar derivatives, such as erythritol, pentaerythritol, arabitol, mannitol, sorbitol, sucrose or glucose. Methylenebisacrylamide is a preferred crosslinking agent.

The homopolymer is preferably used in the form of a nonaqueous polymer dispersion which should have a polymer content not below 30% by weight. Such polymer dispersions are available commercially under the names Salcare® SC 95 (about 50% polymer content, further components: Mineral Oil (INCI name) and tridecylpolyoxypropylene polyoxyethylene ether (INCI name: PPG-1 Trideceth-6)) and Salcare® SC 96 (about 50% polymer content, further components: mixture of diesters of propylene glycol with a mixture of caprylic and capric acid (INCI name: Propylene Glycol Dicaprylate/Dicaprate) and tridecylpolyoxypropylene polyoxyethylene ether (INCI name: PPG-1 Trideceth-6)).

Copolymers with monomer units according to formula (V) contain, as nonionogenic monomer units, preferably acrylamide, methacrylamide, acrylic $C_{1-4}$-alkyl esters and methacrylic $C_{1-4}$-alkyl esters. Of these nonionogenic monomers, the acrylamide is particularly preferred. As described above in the case of the homopolymers, these copolymers too may be crosslinked. A copolymer preferred according to the invention is the crosslinked acrylamide-methacryloyloxyethyltrimethylammonium chloride copolymer. Those copolymers in which the monomers are present in a weight ratio of about 20:80 are available commercially as about 50% strength nonaqueous polymer dispersion under the name Salcare® SC 92.

Further preferred cationic polymers are, for example,
quaternized cellulose derivatives, as are available commercially under the names Celquat® and Polymer JR®. The compounds Celquat® H 100, Celquat® L 200 and Polymer JR® 400 are preferred quaternized cellulose derivatives,
cationic alkyl polyglycosides according to German patent DE 44 13 686,
cationized honey, for example the commercial product Honeyquat® 50,
cationic guar derivatives, such as, in particular, the products sold under the trade names Cosmedia® Guar and Jaguar®,
polysiloxanes with quaternary groups, such as, for example, the commercially available products Q2-7224 (manufacturer: Dow Corning; a stabilized trimethylsilylamodimethicone), Dow Corning® 929 Emulsion (comprising a hydroxylamino-modified silicone, which is also referred to as Amodimethicone), SM-2059 (manufacturer: General Electric), SLM-55067 (manufacturer: Wacker) and Abil®-Quat 3270 and 3272 (manufacturer: Th. Goldschmidt; diquaternary polydimethylsiloxanes, Quaternium-80), polymeric dimethyldiallylammonium salts and copolymers thereof with esters and amides of acrylic acid and methacrylic acid. The products available commercially under the names Merquat® 100 (poly(dimethyldiallylammonium chloride)) and Merquat®550 (dimethyldiallylammonium chloride-acrylamide copolymer) are examples of such cationic polymers, copolymers of vinylpyrrolidone with quaternized derivatives of the dialkylaminoalkyl acrylate and methacrylate, such as, for example, vinylpyrrolidone-dimethylaminoethyl methacrylate copolymers quaternized with diethyl sulfate. Such compounds are available commercially under the names Gafquat® 734 and Gafquat® 755, vinylpyrrolidone-vinylimidazolium methochloride copolymerrs, as are supplied under the names Luviquat® FC 370, FC 550, FC 905 and HM 552, quaternized polyvinyl alcohol, and the polymers with quaternary nitrogen atoms in the polymer main chain known under the names Polyquaternium 2, Polyquaternium 17, Polyquaternium 18 and Polyquaternium 27.

As cationic polymers, it is likewise possible to use the polymers known under the names Polyquaternium-24 (commercial product e.g. Quatrisoft® LM 200). According to the invention, it is likewise possible to use the copolymers of vinylpyrrolidone, as are available as commercial products Copolymer 845 (manufacturer: ISP), Gaffix® VC 713 (manufacturer: ISP), Gafquat® ASCP 1011, Gafquat®HS 110, Luviquat® 8155 and Luviquat® MS 370.

Further cationic polymers according to the invention are the so-called "temporarily cationic" polymers. These polymers usually contain an amino group which, at certain pH values, is in the form of a quaternary ammonium group and thus cationic. Preference is given, for example, to chitosan and derivatives thereof, as are freely available commercially, for example, under the trade names Hydagen® CMF, Hydagen® HCMF, Kytamer® PC and Chitolam® NB/101.

Cationic polymers which are preferred according to the invention are cationic cellulose derivatives and chitosan and derivatives thereof, in particular the commercial products Polymer®JR 400, Hydagen® HCMF and Kytamer® PC, cationic guar derivatives, cationic honey derivatives, in particular the commercial product Honeyquat® 50, cationic alkyl polyglycosides according to German patent DE 44 13 686 and polymers of the Polyquaternium-37 type.

In addition, cationized protein hydrolyzates are also a type of cationic polymer, where the parent protein hydrolyzate can originate from animal, for example from collagen, milk or keratin, from plant, for example from wheat, corn, rice, potatoes, soybean or almonds, from marine life forms, for example from fish collagen or algae, or protein hydrolyzates obtained by biotechnological methods. The protein hydrolyzates forming the basis of the cationic derivatives according to the invention can be obtained from the corresponding proteins by a chemical, in particular alkaline or acidic, hydrolysis, by an enzymatic hydrolysis and/or a combination of the two types of hydrolysis. Hydrolysis of proteins usually gives a protein hydrolyzate with a molecular weight distribution of about 100 daltons up to several thousand daltons. Preference is given to those cationic protein hydrolyzates whose parent protein content has a molecular weight of from 100 up to 25 000 daltons, preferably 250 to 5000 daltons. In addition, cationic protein hydrolyzates are understood as meaning quaternized amino acids and mixtures thereof. Quaternization of the protein hydrolyzates or of the amino acids is often carried out using quaternary ammonium salts, such as, for example, N,N-dimethyl-N-(n-alkyl)-N-(2-hydroxy-3-chloro-n-propyl)ammonium halides. In addition, the cationic protein hydrolyzates can also be derivatized yet further. Typical examples of the cationic protein hydrolyzates and derivatives according to the invention which may be mentioned are the products given under the INCI names in the "International Cosmetic Ingredient Dictionary and Handbook", (seventh edition 1997, The Cosmetic, Toiletry and Fragrance Association 1101 17th Street, N.W., Suite 300, Washington, D.C. 20036-4702) and commercially available: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyl-trimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxy-propyl Hydrolyzed Vegetable Protein, Hydroxypropyl-trimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein.

Very particular preference is given to the vegetable-based cationic protein hydrolyzates and derivatives.

The anionic polymers which can aid the color-retaining action of the active ingredient combination according to the invention are an anionic polymers which have carboxylate and/or sulfonate groups. Examples of anionic monomers of which such polymers can consist are acrylic acid, methacrylic acid, crotonic acid, maleic anhydride and 2-acrylamido-2-methylpropanesulfonic acid. Here, the acidic groups may be completely or partially present as sodium, potassium, ammonium, mono- or triethanolammonium salt. Preferred monomers are 2-acrylamido-2-methylpropanesulfonic acid and acrylic acid.

Anionic polymers which have proven very particularly effective are those which contain, as the sole monomer or comonomer, 2-acrylamido-2-methylpropanesulfonic acid, where the sulfonic acid group can completely or partially be in the form of the sodium, potassium, ammonium, mono- or triethanolammonium salt.

Particular preference is given to the homopolymer of 2-acrylamido-2-methylpropanesulfonic acid, which is commercially available, for example, under the name Rheothik®11-80.

Within this embodiment, it may be preferred to use copolymers of at least one anionic monomer and at least one nonionogenic monomer. With regard to the anionic monomers, reference is made to the substances listed above. Preferred nonionogenic monomers are acrylamide, methacrylamide, acrylic esters, methacrylic esters, vinylpyrrolidone, vinyl ethers and vinyl esters.

Preferred anionic copolymers are acrylic acid-acrylamide copolymers and, in particular, polyacrylamide copolymers with sulfonic acid group-containing monomers. A particularly preferred anionic copolymer consists of 70 to 55 mol % of acrylamide and 30 to 45 mol % of 2-acrylamido-2-methylpropanesulfonic acid, where the sulfonic acid group is completely or partially in the form of the sodium, potassium, ammonium, mono- or triethanolammonium salt. This copolymer can also be in crosslinked form, where the crosslinking agents used are preferably polyolefinically unsaturated compounds such as tetraallyloxyethane, allylsucrose, allylpentaerythritol and methylenebisacrylamide. Such a polymer is present in the commercial product Sepigel®305 from SEPPIC. Use of this compound, which as well as comprising the polymer component, comprises a hydrocarbon mixture ($C_{13}$–$C_{14}$-isoparaffin) and a nonionogenic emulsifier (Laureth-7), has proven particularly advantageous within the scope of the teaching according to the invention.

The sodium acryloyldimethyltaurate copolymers sold under the name Simulgel®600 as a compound with isohexadecane and polysorbate-80 have also proven particularly effective according to the invention.

Likewise preferred anionic homopolymers are uncrosslinked and crosslinked polyacrylic acids. Here, allyl ethers of pentaerythritol, of sucrose and of propylene may be preferred crosslinking agents. Such compounds are commercially available, for example, under the trade name Carbopol®.

Copolymers of maleic anhydride and methyl vinyl ether, in particular those with crosslinking, are likewise color-retaining polymers. A maleic acid-methyl vinyl ether copolymer crosslinked with 1,9-decadiene is commercially available under the name Stabileze® QM.

Further polymers which can be used for increasing the action of the active ingredient combination according to the invention are amphoteric polymers. The term amphoteric polymers covers both those polymers which have both free amino groups and free —COOH or $SO_3H$ groups in the molecule and are capable of forming internal salts, and zwitterionic polymers which contain quaternary ammonium groups and —COO— or —$SO_3^-$ groups in the molecule, and those polymers which contain —COOH or $SO_3H$ groups and quaternary ammonium groups.

One example of an amphopolymer which can be used according to the invention is the acrylic resin obtainable under the name Amphomer®, which represents a copolymer of tert-butylaminoethyl methacrylate, N-(1,1,3,3-tetramethylbutyl)acrylamide and two or more monomers from the group acrylic acid, methacrylic acid and simple esters thereof.

Further amphoteric polymers which can be used according to the invention are the compounds given in British laid-open specification 2 104 091, European laid-open specification 47 714, European laid-open specification 217 274, European laid-open specification 283 817 and German laid-open specification 28 17 369.

Amphoteric polymers which can preferably be used are those polymers which are composed essentially of (a) monomers with quaternary ammonium groups of the general formula (VI),

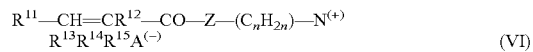

(VI)

in which $R^{11}$ and $R^{12}$, independently of one another, are hydrogen or a methyl group, and $R^{13}$, $R^{14}$ and $R^{15}$, independently of one another, are alkyl groups having 1 to 4 carbon atoms, Z is an NH group or an oxygen atom, n is an integer from 2 to 5 and $A^{(-)}$ is the anion of an organic or inorganic acid and (b) monomeric carboxylic acids of the general formula (VII),

(VII)

in which $R^{16}$ and $R^{17}$, independently of one another, are hydrogen or methyl groups.

These compounds can be used in accordance with the invention either directly or else in salt form, which is obtained by neutralization of the polymers, for example with an alkali metal hydroxide. With regard to the details of the preparation of these polymers, reference is made expressly to the content of German laid-open specification 39 29 973. Very particular preference is given to those polymers in which monomers of type (a) are used in which $R^{13}$, $R^{14}$ and $R^{15}$ are methyl groups, Z is an NH group and $A^{(-)}$ is a halide, methoxysulfate or ethoxysulfate ion; acrylamidopropyl-trimethylammonium chloride is a particularly preferred monomer (a). The monomer (b) used for said polymers is preferably acrylic acid.

According to the invention, it is also possible for the preparations used to comprise two or more, in particular two, different polymers with the same charge and/or in each case an ionic and an amphoteric polymer.

The polymers are present in the compositions used according to the invention preferably in amounts of from 0.05 to 10% by weight, based on the overall composition. Amounts of from 0.1 to 5% by weight, in particular from 0.1 to 3% by weight, are particularly preferred.

The color-retaining action of the active ingredient combination according to the invention can also be increased by a 2-pyrrolidinone-5-carboxylic acid and derivatives thereof. The invention thus further provides for the use of the color-retaining active ingredient combination in combination with derivatives of 2-pyrrolidinone-5-carboxylic acid. Preference is given to the sodium, potassium, calcium, magnesium or ammonium salts in which the ammonium ion carries one to three $C_1$- to $C_4$-alkyl groups in addition to hydrogen. The sodium salt is very particularly preferred. The amounts used in the compositions according to the invention are 0.05 to 10% by weight, based on the overall composition, particularly preferably 0.1 to 5% by weight, and in particular 0.1 to 3% by weight.

In addition, protein hydrolyzates may be present in the preparations used according to the invention. Protein hydrolyzates are product mixtures which are obtained by acidically, basically or enzymatically catalyzed degradation of proteins.

According to the invention, protein hydrolyzates used may either be of vegetable origin or of animal origin.

Animal protein hydrolyzates are, for example, elastin, collagen, keratin, silk and milk protein protein hydrolyzates, which may also be in the form of salts. Such products are sold, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

According to the invention, preference is given to the use of protein hydrolyzates of vegetable origin, e.g. soybean, almond, pea, potato and wheat protein hydrolyzates. Such products are obtainable, for example, under the trade names Gluadin® (Cognis), DiaMin® (Diamalt), Lexein® (Inolex) and Crotein® (Croda).

Even if the use of protein hydrolyzates is preferred as such, it is also possible to use, in their place, amino acid mixtures which may also have been obtained by different methods. Likewise possible is the use of derivatives of protein hydrolyzates, for example in the form of their fatty acid condensation products. Such products are sold, for example, under the names Lamepon® (Cognis), Lexein® (Inolex), Crolastin® (Croda) or Crotein® (Croda).

The protein hydrolyzates or derivatives thereof are present in the compositions used according to the invention preferably in amounts of from 0.1 to 10% by weight, based on the overall composition. Amounts of from 0.1 to 5% by weight are particularly preferred.

The combination of the color-retaining active ingredient combination with surfactants has likewise proven advantageous. In a further preferred embodiment, the compositions used according to the invention comprise surfactants. The term surfactants is understood as meaning surface-active substances which carry an anionic or cationic charge in the molecule. It is also possible for both an anionic and also a cationic charge to be present in the molecule. These zwitterionic or amphoteric surface-active substances can likewise be used according to the invention. In addition, the surface-active substances may also be nonionic.

Suitable anionic surfactants in preparations according to the invention are all anionic surface-active substances suitable for use on the human body. These are characterized by a solubilizing anionic group, such as, for example, a carboxylate, sulfate, sulfonate or phosphate group, and a lipophilic alkyl group having about 8 to 30 carbon atoms. In addition, glycol or polyglycol ether groups, ester, ether and amide groups, and also hydroxyl groups may be present in the molecule. Examples of suitable anionic surfactants are, in each case in the form of the sodium, potassium and ammonium and also the mono-, di- and trialkanolammonium salts having 2 to 4 carbon atoms in the alkanol group, linear and branched fatty acids having 8 to 30 carbon atoms (soaps),
ethercarboxylic acids of the formula R—O—($CH_2$—$CH_2O$)$_x$—$CH_2$—COOH in which R is a linear alkyl group having 8 to 30 carbon atoms and x=0 or 1 to 16,
acyl sarcosides having 8 to 24 carbon atoms in the acyl group,
acyl taurides having 8 to 24 carbon atoms in the acyl group,
acyl isethionates having 8 to 24 carbon atoms in the acyl group,
sulfosuccinic mono- and dialkyl esters having 8 to 24 carbon atoms in the alkyl group and sulfosuccinic monoalkyl polyoxyethyl esters having 8 to 24 carbon atoms in the alkyl group and 1 to 6 oxyethyl groups,
linear alkanesulfonates having 8 to 24 carbon atoms,
linear alpha-olefinsulfonates having 8 to 24 carbon atoms,
alpha-sulfofatty acid methyl esters of fatty acids having 8 to 30 carbon atoms,
alkyl sulfates and alkyl polyglycol ether sulfates of the formula R—O($CH_2$—$CH_2O$)$_x$—$OSO_3H$ in which R is a preferably linear alkyl group having 8 to 30 carbon atoms and x=0 or 1 to 12,
mixtures of surface-active hydroxysulfonates according to DE-A-37 25 030,
sulfated hydroxyalkyl polyethylene and/or hydroxy-alkylene propylene glycol ethers according to DE-A-37 23 354,
sulfonates of unsaturated fatty acids having 8 to 24 carbon atoms and 1 to 6 double bonds according to DE-A-39 26 344,
esters of tartaric acid and citric acid with alcohols, which represent addition products of about 2–15 molecules of ethylene oxide and/or propylene oxide onto fatty alcohols having 8 to 22 carbon atoms,
alkyl and/or alkenyl ether phosphates of the formula (VIII)

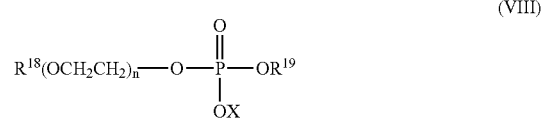

in which $R^{18}$ is preferably an aliphatic hydrocarbon radical having 8 to 30 carbon atoms, $R^{19}$ is hydrogen, a radical ($CH_2CH_2O$)$_n R^{18}$ or X, n is numbers from 1 to 10 and X is hydrogen, an alkali metal or alkaline earth metal or $NR^{20}R^{21}R^{22}R^{23}$ where $R^{20}$ to $R^{23}$, independently of one another, are hydrogen or a $C_1$ to $C_4$-hydrocarbon radical,
sulfated fatty acid alkylene glycol esters of the formula (IX)

in which $R^{24}CO$— is a linear or branched, aliphatic, saturated and/or unsaturated acyl radical having 6 to 22 carbon atoms, Alk is $CH_2CH_2$, $CHCH_3CH_2$ and/or $CH_2CHCH_3$, n is numbers from 0.5 to 5 and M is a cation, as are described in DE-A 197 36 906.5,
monoglyceride sulfates and monoglyceride ether sulfates of the formula (X)

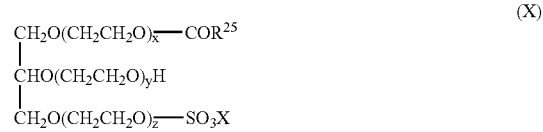

in which $R^{25}CO$ is a linear or branched acyl radical having 6 to 22 carbon atoms, x, y and z are in total 0 or numbers from 1 to 30, preferably 2 to 10, and X is an alkali metal or alkaline earth metal. Typical examples of monoglyceride (ether) sulfates suitable for the purposes of the invention are the reaction products of lauric acid monoglyceride, coconut fatty acid monoglyceride, palmitic acid monoglyceride, stearic acid monoglyceride, oleic acid monoglyceride and tallow fatty acid monoglyceride, and also ethylene oxide adducts thereof with sulfur trioxide or chlorosulfonic acid in the form of its sodium salts. Preference is given to using monoglyceride sulfates of the formula (X) in which $R^2 1CO$ is a linear acyl radical having 8 to 18 carbon atoms, as have been described, for example, in EP-B1 0 561 825, EP-B1 0 561 999, DE-A1 42 04 700 or by A. K. Biswas et al. in J. Am. Oil Chem. Soc. 37, 171 (1960) and F. U. Ahmed in J. Am. Oil Chem. Soc. 67, 8 (1990).

Preferred anionic surfactants are alkyl sulfates, alkylpolyglycol ether sulfates and ethercarboxylic acids having 10 to 18 carbon atoms in the alkyl group and up to 12 glycol ether groups in the molecule and sulfosuccinic mono- and dialkyl esters having 8 to 18 carbon atoms in the alkyl group and sulfosuccinic monoalkyl polyoxyethyl esters having 8 to 18 carbon atoms in the alkyl group and 1 to 6 oxyethyl groups.

Zwitterionic surfactants is the term used to describe those surface-active compounds which carry at least one quaternary ammonium group and at least one $—COO^{(-)}$ or $—SO^3{}^{(-)}$ group in the molecule. Particularly suitable zwitterionic surfactants are the so-called betaines, such as N-alkyl-N,N-dimethylammonium glycinates, for example cocoalkyldimethylammonium glycinate, N-acyl-aminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl carboxymethylglycinate. A preferred zwitterionic surfactant is the fatty acid amide derivative known under the INCI name Cocamidopropyl Betaine.

Ampholytic surfactants are understood as meaning those surface-active compounds which, apart from a $C_8$–$C_{24}$-alkyl or -acyl group in the molecule, contain at least one free amino group and at least one $—COOH$ or $—SO_3H$ group and are capable of forming internal salts. Examples of suitable ampholytic surfactants are N-alkylglycines, N-alkylpropionic acids, N-alkylamino-butyric acids, N-alkyliminodipropionic acids, N-hydroxyethyl-N-alkylamidopropylglycines, N-alkyl-taurines, N-alkylsarcosines, 2-alkylaminopropionic acids and alkylaminoacetic acids having in each case about 8 to 24 carbon atoms in the alkyl group.

Particularly preferred ampholytic surfactants are N-cocoyl aminopropionate, cocoacyl aminoethylamino-propionate and $C_{12}$–$C_{18}$-acylsarcosine.

Nonionic surfactants contain, as hydrophilic group, e.g. a polyol group, a polyalkylene glycol ether group or a combination of polyol and polyglycol ether group. Such compounds are, for example, addition products of from 2 to 50 mol of ethylene oxide and/or 0 to 5 mol of propylene oxide onto linear and branched fatty alcohols having 8 to 30 carbon atoms, onto fatty acids having 8 to 30 carbon atoms and onto alkylphenols having 8 to 15 carbon atoms in the alkyl group, addition products, terminally capped with a methyl or $C_2$–$C_6$-alkyl radical, of from 2 to 50 mol of ethylene oxide and/or 0 to 5 mol of propylene oxide onto linear and branched fatty alcohols having 8 to 30 carbon atoms, onto fatty acids having 8 to 30 carbon atoms and onto alkylphenols having 8 to 15 carbon atoms in the alkyl group, such as, for example, the products obtainable under the trade names Dehydol® LS, Dehydol® LT (Cognis), $C_{12}$–$C_{30}$-fatty mono- and diesters of addition products of from 1 to 30 mol of ethylene oxide onto glycerol, addition products of from 5 to 60 mol of ethylene oxide onto castor oil and hydrogenated castor oil, polyol fatty acid esters, such as, for example, the commercial product Hydagen® HSP (Cognis) or Sovermol products (Cognis), alkoxylated triglycerides, alkoxylated fatty alkyl esters of the formula (XI)

$$R^{26}CO—(OCH_2CHR^{27})_w OR^{28} \qquad (XI)$$

in which $R^{26}CO$ is a linear or branched, saturated and/or unsaturated acyl radical having 6 to 22 carbon atoms, $R^{27}$ is hydrogen or methyl, $R^{28}$ is linear or branched alkyl radicals having 1 to 4 carbon atoms and w is numbers from 1 to 20, amine oxides, hydroxy mixed ethers, as are described, for example, in DE-A 19738866, sorbitan fatty acid esters and addition products of ethylene oxide onto sorbitan fatty acid esters, such as, for example, the polysorbates, sugar fatty acid esters and addition products of ethylene oxide onto sugar fatty acid esters, addition products of ethylene oxide onto fatty acid alkanolamides and fatty amines, fatty acid N-alkylglucamides, Preferred nonionic surfactants have proven to be the alkylene oxide addition products onto saturated linear fatty alcohols and fatty acids having in each case 2 to 30 mol of ethylene oxide per mole of fatty alcohol or fatty acid. Preparations with excellent properties are likewise obtained if they comprise, as nonionic surfactants, fatty acid esters of ethoxylated glycerol.

These compounds are characterized by the following parameters. The alkyl radical R contains 6 to 22 carbon atoms and may either be linear or branched. Preference is given to primary linear aliphatic radicals and aliphatic radicals methyl-branched in the 2-position. Such alkyl radicals are, for example, 1-octyl, 1-decyl, 1-lauryl, 1-myristyl, 1-cetyl and 1-stearyl. Particular preference is given to 1-octyl, 1-decyl, 1-lauryl, 1-myristyl. If so-called "oxo alcohols" are used as starting materials, compounds with an odd number of carbon atoms in the alkyl chain predominate.

The compounds containing alkyl groups used as surfactant may in each case be uniform substances. It is, however, usually preferred to start, in the preparation of these substances, from native vegetable or animal raw materials, thus giving mixtures of substances with different alkyl chain lengths dependent on the raw material in question.

For the surfactants which represent addition products of ethylene oxide and/or propylene oxide onto fatty alcohols or derivatives of these addition products, it is possible to use either products with a "normal" homolog distribution, or those with a narrowed homolog distribution. "Normal" homolog distribution is understood as meaning here mixtures of homologs which are obtained in the reaction of fatty alcohol and alkylene oxide using alkali metals, alkali metal hydroxides and alkali metal alkoxides as catalysts. Narrowed homolog distributions are obtained, by contrast, when, for example, hydrotalcites, alkaline earth metal salts of ethercarboxylic acids, alkaline earth metal oxides, hydroxides or alkoxides are used as catalysts. The use of products with narrowed homolog distribution may be preferred.

These surfactants are used in amounts of 0.1–45% by weight, preferably 1–30% by weight and very particularly preferably 1–15% by weight, based on the total compositions used according to the invention.

According to the invention, it is likewise possible to use cationic surfactants of the quaternary ammonium compound type, the ester quat type and the amidoamine type. Preferred quaternary ammonium compounds are ammonium halides, in particular chlorides and bromides, such as alkyltrimethylammonium chlorides, dialkyl-dimethylammonium chlorides and trialkylmethylammonium chlorides, e.g. cetyltrimethylammonium chloride, stearyltrimethylammonium chloride, distearyldimethyl-ammonium chloride, lauryldimethylammonium chloride, lauryldimethylbenzylammonium chloride and tricetyl-methylammonium chloride, and the imidazolium compounds known under the INCI names Quaternium-27 and Quaternium-83. The long alkyl chains of the abovementioned surfactants preferably have 10 to 18 carbon atoms.

Ester quats are known substances which contain either at least one ester function or at least one quaternary ammonium group as structural element. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the trade names Stepantex®, Dehyquart® and Armocare®. The products Armocare® VGH-70, a N,N-bis (2-palmitoyloxy-ethyl)dimethylammonium chloride, and also Dehyquart® F-75, Dehyquart® C-4046, Dehyquart® L80 and Dehyquart® AU-35 are examples of such ester quats.

The alkylamidoamines are usually prepared by amidation of natural or synthetic fatty acids and fatty acid cuts with dialkylaminoamines. A particularly suitable compound from this group of substances according to the invention is the stearamidopropyldimethylamine available commercially under the name Tegoamid® S 18.

The cationic surfactants are present in the compositions used according to the invention preferably in amounts of from 0.05 to 10% by weight, based on the overall composition. Amounts of from 0.1 to 5% by weight are particularly preferred.

Anionic, nonionic, zwitterionic and/or amphoteric surfactants and mixtures thereof may be preferred according to the invention.

In a further preferred embodiment, the action of the active ingredient according to the invention can be increased by emulsifiers. Such emulsifiers, are, for example:
- addition products of from 4 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group,
- $C_{12}$–$C_{22}$-fatty acid mono- and diesters of addition products of from 1 to 30 mol of ethylene oxide onto polyols having 3 to 6 carbon atoms, in particular onto glycerol,
- ethylene oxide and polyglycerol addition products onto methyl glucoside fatty acid esters, fatty acid alkanolamides and fatty acid glucamides,
- $C_8$–$C_{22}$-alkyl mono- and oligoglycosides and ethoxylated analogs thereof, where degrees of oligomerization of from 1.1 to 5, in particular 1.2 to 2.0, and glucose as sugar component are preferred,
- mixtures of alkyl (oligo) glucosides and fatty alcohols, for example the commercially available product Montanov® 68,
- addition products of from 5 to 60 mol of ethylene oxide onto castor oil and hydrogenated castor oil,
- partial esters of polyols having 3–6 carbon atoms with saturated fatty acids having 8 to 22 carbon atoms,
- sterols. Sterols are understood as meaning a group of steroids which carry a hydroxyl group on the 3rd carbon atom of the steroid backbone and are isolated both from animal tissue (zoosterols) and from vegetable fats (phytosterols). Examples of zoosterols are cholesterol and lanosterol. Examples of suitable phytosterols are ergosterol, stigmasterol and sitosterol. Sterols are also isolated from fungi and yeasts, these being termed micosterols.
- Phospholipids. These are understood as meaning primarily the glucose phospholipids which are obtained, for example, as lecithins or phosphatidylcholines from, for example, egg yolk or plant seeds (e.g. soybeans).
- Fatty acid esters of sugars and sugar alcohols, such as sorbitol
- polyglycerols and polyglycerol derivatives, such as, for example, polyglycerol poly-12-hydroxy-stearate (commercial product Dehymuls® PGPH)
- linear and branched fatty acids having 8 to 30 carbon atoms and their Na, K, ammonium, Ca, Mg and Zn salts.

The compositions according to the invention comprise the emulsifiers preferably in amounts of 0.1–25% by weight, in particular 0.5–15% by weight, based on the overall composition.

Preferably, the compositions according to the invention can comprise at least one nonionic emulsifier with an HLB value of from 8 to 18, according to the definitions given in Römpp Lexikon Chemie (Ed. J. Falbe, M. Regitz), 10th edition, Georg Thieme Verlag Stuttgart, New York, (1997), page 1764. Nonionogenic emulsifiers with a HLB value of 10–15 may be particularly preferred according to the invention.

It has likewise proven advantageous to combine the color-retaining active ingredient combination with vitamins, provitamins and vitamin precursors and derivatives thereof.

In this connection, according to the invention, preference is given to those vitamins, provitamins and vitamin precursors which are usually assigned to the groups A, B, C, E, F and H.

The group of substances referred to as vitamin A include retinol (vitamin $A_1$) and 3,4-didehydroretinol (vitamin $A_2$). β-carotene is the provitamin of retinol. Suitable as vitamin A component are, according to the invention, for example vitamin A acid and esters thereof, vitamin A aldehyde and vitamin A alcohol, and esters thereof, such as the palmitate and the acetate. The preparations used according to the invention comprise the vitamin A component preferably in amounts of 0.05–1% by weight, based on the overall preparation.

The vitamin B group or the vitamin B complex include, inter alia,
vitamin $B_1$ (thiamine)
vitamin $B_2$ (riboflavin)
vitamin $B_3$. Under this term are often listed the compounds nicotinic acid and nicotinamide (niacinamide). According to the invention, preference is given to nicotinamide, which is present in the compositions used according to the invention preferably in amounts of from 0.05 to 1% by weight, based on the overall composition.

vitamin $B_5$ (pantothenic acid and panthenol). Within this group, preference is given to using panthenol. Derivatives of panthenol which can be used according to the invention are, in particular, the esters and ethers of panthenol, and also cationically derivatized panthenols. Individual representatives are, for example, panthenol triacetate, panthenol monoethyl ether and its monoacetate, and the cationic panthenol derivatives disclosed in WO 92/13829. Said compounds of the vitamin $B_5$ type are present in the compositions used according to the invention preferably in amounts of 0.05–10% by weight, based on the overall composition. Amounts of 0.1–5% by weight are particularly preferred.

vitamin $B_6$ (pyridoxine and pyridoxamine and pyridoxal).

Vitamin C (ascorbic acid). Vitamin C is used in the compositions used according to the invention preferably in amounts of from 0.1 to 3% by weight, based on the overall composition. The use in the form of the palmitic ester, the glucosides or phosphates may be preferred. The use in combination with tocopherols may likewise be preferred.

Vitamin E (tocopherols, in particular α-tocopherol). Tocopherol and its derivatives, which covers, in particular, the esters, such as the acetate, the nicotinate, the phosphate and the succinate, are present in the compositions used according to the invention preferably in amounts of 0.05–1% by weight, based on the overall composition.

Vitamin F. The term "vitamin F" is usually understood as meaning essential fatty acids, in particular linoleic acid, linolenic acid and arachidonic acid.

Vitamin H. Vitamin H is used to refer to the compound (3aS,4S,6aR)-2-oxohexahydrothienol[3,4-d]imidazole-4-valeric acid, which has in the meantime become known by the trivial name biotin. Biotin is present in the compositions used according to the invention preferably in amounts of from 0.0001 to 1.0% by weight, in particular in amounts of from 0.001 to 0.01% by weight.

The compositions used according to the invention preferably comprise vitamins, provitamins and vitamin precursors from the groups A, B, E and H.

Panthenol and its derivatives and also nicotinamide and biotin are particularly preferred.

Finally, the action of the color-retaining active ingredient combination can also be increased through the combined use of plant extracts.

Usually, these extracts are prepared by extraction of the whole plant. However, it may also be preferred in individual cases to prepare the extracts exclusively from flowers and/or leaves of the plant.

With regard to the plant extracts which can be used according to the invention, reference is made in particular to the extracts which are listed in the table starting on page 44 of the 3rd edition of the introduction to the ingredient declaration of cosmetic products, published by the Industrieverband Körperpflege- und Waschmittel e.V. (IKW), Frankfurt.

According to the invention, the extracts from green tea, oak bark, stinging nettle, hamamelis, hops, chamomile, burdock, horsetail, whitethorn, linden blossom, almond, aloe vera, spruce needle, horse chestnut, sandalwood, juniper, coconut, mango, apricot, lemon, wheat, kiwi, melon, orange, grapefruit, sage, rosemary, birch, mallow, lady's-smock, wild thyme, yarrow, thyme, melissa, restharrow, coltsfoot, marshmallow, meristem, ginseng and root ginger, in particular, are preferred.

Particular preference is given to the extracts from green tea, oak bark, stinging nettle, hamamelis, hops, chamomile, burdock, horsetail, linden blossom, almond, aloe vera, coconut, mango, apricot, lemon, wheat, kiwi, melon, orange, grapefruit, sage, rosemary, birch, lady's-smock, wild thyme, yarrow, restharrow, meristem, ginseng and root ginger.

Very particularly suitable for the use according to the invention are the extracts from green tea, almond, aloe vera, coconut, mango, apricot, lemon, wheat, kiwi and melon.

The extractants used for the preparation of said plant extracts may be water, alcohols and mixtures thereof. Of the alcohols, preference is given in this connection to lower alcohols, such as ethanol and isopropanol, but in particular polyhydric alcohols, such as ethylene glycol and propylene glycol, both as a sole extractant and also in a mixture with water. Plant extracts based on water/propylene glycol in the ratio 1:10 to 10:1 have proven particularly suitable.

According to the invention, the plant extracts can be used both in pure form and also in dilute form. If they are used in dilute form, they usually comprise about 2–80% by weight of active substance and, as solvent, the extractant or extractant mixture used in their isolation.

In addition, it may be preferred to use mixtures of two or more, in particular two, different plant extracts in the compositions according to the invention.

The color-retaining active ingredient combination according to the invention can in principle be added directly to the colorant. However, the application of the color-retaining active ingredient combination onto the colored keratin fiber can also be carried out in a separate step, either before or after the actual coloring operation. Separate treatments, where necessary including days or weeks before or after the coloring operation, are also covered by the teaching according to the invention. However, application of the active ingredient combination according to the invention is preferably carried out prior to coloring and, in particular, in the colorant.

The term "coloring operation" covers here all methods known to the person skilled in the art in which a colorant is applied to, optionally dampened, hair, and is either left on the hair for a period of between a few minutes and about 45 minutes and then rinsed out with water or a surfactant-containing composition, or is left on the hair altogether. In this connection, reference is made expressly to the known monographs, e.g. Kh. Schrader, Grundlagen und Rezepturen der Kosmetika [Principles and formulations of cosmetics], 2nd edition, Hüthig Buch Verlag, Heidelberg, 1989, which report the corresponding knowledge of the person skilled in the art.

With regard to the manner with which the color-retaining active ingredient combination according to the invention is applied to the keratin fiber, in particular to human hair, no principle limitations exist. Suitable formulation forms of these preparations are, for example, creams, lotions, solutions, tonics, emulsions, such as W/O, O/W, PIT emulsions (emulsions according to the teaching of phase inversion, termed PIT), microemulsions and multiple emulsions, gels, sprays, aerosols and foam aerosols. The pH of these preparations may in principle be from 2–11. It is preferably between 5 and 11, values from 6 to 10 being particularly preferred. To set the pH, virtually any acid or base which can be used for cosmetic purposes can be used. Usually, the acids used are food acids. Food acids are understood as meaning those acids which are consumed in the course of usual eating and have positive effects on the human organism. Food acids are, for example, acetic acid, lactic acid, tartaric acid, citric acid, malic acid, ascorbic acid and gluconic acid. For the purposes of the invention, the use of citric acid and lactic acid is particularly preferred. Preferred bases are ammonia, alkali metal hydroxides, monoethanolamine, triethanolamine and N,N,N',N'-tetrakis(2-hydroxypropyl)ethylenediamine.

Preparations which remain on the hair have proven particularly effective and can therefore represent preferred embodiments of the teaching according to the invention. "Remaining on the hair" is understood according to the invention as meaning those preparations which, in the course of treatment, are not rinsed out of the hair again after a period of from a few seconds to one hour using water or an aqueous solution. Instead, the preparations remain on the hair until the next hair washing, i.e. usually more than 12 hours.

According to a preferred embodiment, these preparations are formulated as hair treatment or hair conditioner. The preparations of the invention according to this embodiment can, following expiry of this contact time, be rinsed out with water or an at least predominantly water-containing composition; however, as stated above, they are preferably left on the hair. In this connection, it may be preferred to apply the preparation according to the invention to the hair prior to the application of a cleaning composition, a waving composition or other hair-treatment compositions. In this case, the preparation according to the invention serves as color protection for the subsequent applications.

According to further embodiments, the compositions according to the invention may, however, also, for example, be cleaning compositions such as shampoos, care compositions such as rinses, setting compositions such as hair-setting compositions, setting foams, styling gels and low-waving compositions, permanent shaping compositions, such as permanent-waving and neutralization compositions and pretreatment compositions or afterrinses used in particular in the course of a permanent-waving process or coloring process.

In addition to the color-retaining active ingredient combination obligatorily required according to the invention and the further abovementioned preferred components, these preparations may in principle comprise all other components known to the person skilled in the art for such cosmetic compositions.

Further active ingredients, auxiliaries and additives are, for example,
- nonionic polymers, such as, for example, vinyl-pyrrolidone/vinyl acrylate copolymers, polyvinyl-pyrrolidone and vinylpyrrolidone/vinyl acetate copolymers and polysiloxanes,
- thickeners, such as agar agar, guar gum, alginates, xanthan gum, gum arabic, karaya gum, carob bean flour, linseed gums, dextrans, cellulose derivatives, e.g. methylcellulose, hydroxyalkylcellulose and carboxymethylcellulose, starch fractions and derivatives, such as amylose, amylopectin and dextrins, clays such as, for example, bentonite or fully synthetic hydrocolloids, such as, for example, polyvinyl alcohol,
- structurants, such as maleic acid and lactic acid,
- hair-conditioning compounds, such as phospho-lipids, for example soya lecithin, egg lecithin and cephalins, and silicone oils,
- perfume oils, dimethyl isosorbide and cyclodextrins,
- solvents and solubility promoters, such as ethanol, isopropanol, ethylene glycol, propylene glycol and diethylene glycol,
- symmetrical and asymmetrical linear and branched dialkyl ethers having a total of between 12 and 36 carbon atoms, in particular 12 and 24 carbon atoms, such as, for example, di-n-octyl ether, di-n-decyl ether, di-n-nonyl ether, di-n-undecyl ether and di-n-dodecyl ether, n-hexyl n-octyl ether, n-octyl n-decyl ether, n-decyl n-undecyl ether, n-undecyl n-dodecyl ether and n-hexyl n-undecyl ether, and di-tert-butyl ether, diisopentyl ether, di-3-ethyl-decyl ether, tert-butyl n-octyl ether, isopentyl n-octyl ether and 2-methylpentyl n-octyl ether,
- fatty alcohols, in particular linear and/or saturated fatty alcohols having 8 to 30 carbon atoms, and monoesters of the fatty acids with alcohols having 6 to 24 carbon atoms,
- fiber structure-improving active ingredients, in particular mono-, di- and oligosaccharides, such as, for example, glucose, galactose, fructose, fruit sugar and lactose,
- conditioning active ingredients, such as paraffin oils, vegetable oils, e.g. sunflower oil, orange oil, almond oil, wheatgerm oil and peach kernel oil, and phospholipids, for example soya lecithin, egg lecithin and cephalins,
- quaternized amines, such as methyl-1-alkylamido-ethyl-2-alkylimidazolinium methosulfate
- defoamers, such as silicones,
- dyes for coloring the composition,
- antidandruff active ingredients, such as piroctone olamine, zinc omadine and climbazole,
- light protection agents, in particular derivatized benzophenones, cinnamic acid derivatives and triazines,
- further substances for setting the pH, such as, for example, α- and β-hydroxycarboxylic acids
- active ingredients, such as allantoin and bisabolol,
- cholesterol,
- bodying agents, such as sugar esters, polyol esters or polyol alkyl ethers,
- fats and waxes, such as spermaceti, beeswax, montan wax and paraffins,
- fatty acid alkanolamides,
- complexing agents, such as EDTA, NTA, β-alanine-diacetic acid and phosphonic acids,
- swelling and penetration substances, such as glycerol, propylene glycol monoethyl ether, carbonates, hydrogencarbonates, guanidines, ureas, and primary, secondary and tertiary phosphates,
- opacifiers, such as latex, styrene/PVP and styrene/acrylamide copolymers
- pearlizing agents, such as ethylene glycol mono- and distearate and PEG-3 distearate,
- pigments,
- reducing agents, such as, for example, thioglycolic acid and derivatives thereof, thiolactic acid, cysteamine, thiomalic acid and α-mercaptoethanesulfonic acid,
- propellants, such as propane-butane mixtures, $N_2O$, dimethyl ether, $CO_2$ and air,
- antioxidants.

With regard to further optional components and the amounts of these components used, reference is expressly made to the relevant handbooks known to the person skilled in the art, e.g. the above mentioned monograph by Kh. Schrader.

As already mentioned above, within the scope of the teaching according to the invention, it may be preferred to incorporate the color-retaining active ingredient combination directly into the colorant or tint.

The composition of the colorant or tint is not subject to any limitations in principle.

As dye (precursor), it is possible, to use
oxidation dye precursors of the developer and coupler type,
natural and synthetic direct dyes and
precursors of nature-analogous dyes, such as indole and indoline derivatives, and mixtures of representatives of one or more of these groups.

The oxidation dye precursors of the developer type customarily used are primary aromatic amines with a further free or substituted hydroxyl or amino group situated in the para or ortho position, diaminopyridine derivatives, heterocyclic hydrazones, 4-aminopyrazole derivatives, and 2,4,5,6-tetraminopyrimidine and derivatives thereof. Suitable developer components are, for example, p-phenylenediamine, p-tolylenediamine, p-aminophenol, o-aminophenol, 1-(2'-hydroxyethyl)-2,5-diaminobenzene, N,N-bis(2-hydroxyethyl)-p-phenylene-diamine, 2-(2,5-diaminophenoxy)ethanol, 4-amino-3-methylphenol, 2,4,5,6-tetraminopyrimidine, 2-hydroxy-4,5,6-triaminopyrimidine, 4-hydroxy-2,5,6-triamino-pyrimidine, 2,4-dihydroxy-5,6-diaminopyrimidine, 2-di-methylamino-4,5,6-triaminopyrimidine, 2-hydroxymethyl-amino-4-aminophenol, bis(4-aminophenyl)amine, 4-amino-3-fluorophenol, 2-aminomethyl-4-aminophenol, 2-hydroxymethyl-4-aminophenol, 4-amino-2-((diethylamino)methyl)phenol, bis(2-hydroxy-5-aminophenyl)methane, 1,4-bis(4-aminophenyl)diazacycloheptane, 1,3-bis(N(2-hydroxyethyl)-N(4-aminophenylamino))-2-propanol, 4-amino-2-(2-hydroxyethoxy)phenol, 1,10-bis(2,5-diaminophenyl)-1,4,7,10-tetraoxadecane, and 4,5-diaminopyrazole derivatives as claimed in EP 0 740 741 and WO 94/08970, such as, for example, 4,5-diamino-1-(2'-hydroxyethyl)-pyrazole. Particularly advantageous developer components are p-phenylenediamine, p-tolylenediamine, p-aminophenol, 1-(2'-hydroxyethyl)-2,5-diaminobenzene, 4-amino-3-methylphenol, 2-aminomethyl-4-aminophenol, 2,4,5,6-tetraminopyrimidine, 2-hydroxy-4,5,6-triamino-pyrimidine, 4-hydroxy-2,5,6-triaminopyrimidine.

Oxidation dye precursors of the coupler type which are used are usually m-phenylenediamine derivatives, naphthols, resorcinol and resorcinol derivatives, pyrazolones and m-aminophenol derivatives. Examples of such coupler components are m-aminophenol and derivatives thereof such as, for example, 5-amino-2-methylphenol, 5-(3-hydroxy-propylamino)-2-methylphenol, 3-amino-2-chloro-6-methylphenol, 2-hydroxy-4-aminophenoxyethanol, 2,6-dimethyl-3-aminophenol, 3-trifluoroacetyl-amino-2-chloro-6-methylphenol, 5-amino-4-chloro-2-methylphenol, 5-amino-4-methoxy-2-methylphenol, 5-(2'-hydroxyethyl)amino-2-methylphenol, 3-(di-ethylamino)phenol, N-cyclopentyl-3-aminophenol, 1,3-dihydroxy-5-(methylamino)benzene, 3-(ethyl-amino)-4-methylphenol and 2,4-dichloro-3-aminophenol, o-aminophenol and derivatives thereof, m-diaminobenzene and derivatives thereof, such as, for example, 2,4-diaminophenoxyethanol, 1,3-bis(2,4-diaminophenoxy)propane, 1-methoxy-2-amino-4-(2'-hydroxyethylamino)benzene, 1,3-bis(2,4-diaminophenyl) propane, 2,6-bis(2-hydroxyethyl-amino)-1-methylbenzene and 1-amino-3-bis(2'-hydroxyethyl)aminobenzene, o-diaminobenzene and derivatives thereof, such as, for example, 3,4-diaminobenzoic acid and 2,3-diamino-1-methylbenzene, di- or trihydroxybenzene derivatives, such as, for example, resorcinol, resorcinolmonomethyl ether, 2-methylresorcinol, 5-methylresorcinol, 2,5-di-methylresorcinol, 2-chlororesorcinol, 4-chloro-resorcinol, pyrogallol and 1,2,4-trihydroxybenzene, pyridine derivatives, such as, for example, 2,6-dihydroxypyridine, 2-amino-3-hydroxypyridine, 2-amino-6-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives, such as, for example, 1-naphthol, 2-methyl-1-naphthol, 2-hydroxymethyl-1-naphthol, 2-hydroxyethyl-1-naphthol, 1,5-di-hydroxynaphthalene, 1,6-dihydroxynaphthalene, 1,7-dihydroxynaphthalene, 1,8-dihydroxynaph-thalene, 2,7-dihydroxynaphthalene and 2,3-di-hydroxynaphthalene, morpholine derivatives, such as, for example, 6-hydroxybenzomorpholine and 6-aminobenzomorph-oline, quinoxaline derivatives, such as, for example, 6-methyl-1,2,3,4-tetrahydroquinoxaline, pyrazole derivatives, such as, for example, 1-phenyl-3-methylpyrazol-5-one, indole derivatives, such as, for example, 4-hydroxyindole, 6-hydroxyindole and 7-hydroxy-indole, methylenedioxybenzene derivatives, such as, for example, 1-hydroxy-3,4-methylenedioxybenzene, 1-amino-3,4-methylenedioxybenzene and 1(2 hydroxyethyl)amino-3,4-methylenedioxybenzene, Particularly suitable coupler components are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-di-hydroxy-3,4-dimethylpyridine.

Direct dyes are usually nitrophenylenediamines, nitroaminophenols, azo dyes, anthraquinones or indophenols. Particularly suitable direct dyes are the compounds known under the international names or trade names HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17, and 1,4-bis (β-hydroxyethyl)amino-2-nitro-benzene, 4-amino-2-nitrodiphenylamine-2'-carboxylic acid, 6-nitro-1,2,3,4-tetrahydroquinoxaline, hydroxy-ethyl-2-nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene.

Naturally occurring direct dyes are, for example, henna red, henna neutral, henna black, chamomile blossom, sandalwood, black tea, buckthorn bark, sage, logwood, madder root, catechu, cedar and alkanna root.

It is not necessary for the oxidation dye precursors or the direct dyes to each represent uniform compounds. Rather, it is possible that, as a result of the preparation processes for the individual dyes, further components are present in minor amounts in the hair colorants according to the invention, provided that these do not adversely affect the coloring result, or have to be excluded for other reasons, e.g. toxicological reasons.

With regard to the dyes which can be used in the hair colorants and tints according to the invention, reference is also made expressly to the monograph by Ch. Zviak, The Science of Hair Care, chapter 7 (pages 248–250; direct dyes), and chapter 8, pages 264–267; oxidation dye precursors), published as volume 7 of the series "Dermatology" (Ed. Ch., Culnan and H. Maibach), Verlag Marcel Dekker Inc., New York, Basle, 1986, and the "European Inventory of Cosmetic Raw Materials", published by the European Commission, available in diskette format from the Bundesverband Deutscher Industrie- und Handelsunternehmen für Arzneimittel, Reformwaren und Körperpflegemittel e.V., Mannheim.

The precursors of nature-analogous dyes used are, for example, indoles and indolines, and their physiologically compatible salts. Preference is given to those indoles and indolines which have at least one hydroxyl or amino group, preferably as substituent on the six-membered ring. These groups can carry further substituents, e.g. in the form of an etherification or esterification of the hydroxyl group or an alkylation of the amino group. Particularly advantageous properties are shown by 5,6-dihydroxyindoline, N-methyl-5,6-dihydroxyindoline, N-ethyl-5,6-dihydroxy-indoline, N-propyl-5,6-dihydroxyindoline, N-butyl-5,6-dihydroxyindoline, 5,6-dihydroxyindoline-2-carboxylic acid, 6-hydroxyindoline, 6-aminoindoline and 4-amino-indoline, and 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, particular emphasis is given to N-methyl-5,6-dihydroxyindoline, N-ethyl-5,6-dihydroxy-indoline, N-propyl-5,6-dihydroxyindoline, N-butyl-5,6-dihydroxyindoline and, in particular, 5,6-dihydroxy-indoline and N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxy-indole.

The indoline and indole derivatives in the colorants used for the purposes of the method according to the invention [lacuna] be used either as free bases or else in the form of their physiologically compatible salts with inorganic or organic acids, e.g. the hydrochlorides, the sulfates and hydrobromides.

When using dye precursors of the indoline or indole type, it may be preferred to use these together with at least one amino acid and/or at least one oligopeptide. Preferred aminoacids are aminocarboxylic acids, in particular α-aminocarboxylic acids and ω-aminocarboxylic acids. Of the α-aminocarboxylic acids, particular preference is given in turn to arginine, lysine, ornithine and histidine. A very particularly preferred amino acid is arginine, in particular in free form, but also used as the hydrochloride.

Hair colorants, particularly if the coloration is carried out oxidatively, whether with atmospheric oxygen or other oxidizing agents such as hydrogen peroxide, are usually adjusted to be slightly acidic to alkaline, i.e. to pH values in the range from about 5 to 11. For this purpose, the colorants comprise alkalinizing agents, usually alkali metal or alkaline earth metal hydroxides, ammonia or organic amines. Preferred alkalinizing agents are monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol and triethanol-amine, and also alkali metal and alkaline earth metal hydroxides. In particular, monoethanolamine, triethanolamine and 2-amino-2-methylpropanol and 2-amino-2-methyl-1,3-propanediol are preferred within this group. The use of ω-amino acids, such as ω-amino-caproic acid, as alkalinizing agent is also possible.

If the actual hair colors are formed in the course of an oxidative process, then customary oxidizing agents, such as, in particular, hydrogen peroxide or addition products thereof onto urea, melamine or sodium borate, can be used. The oxidation with atmospheric oxygen as the sole oxidizing agent may, however, be preferred. In addition, it is possible to carry out the oxidation using enzymes, where the enzymes are used both for generating oxidizing percompounds, and also for intensifying the action of a small amount of oxidizing agents present, or else enzymes are used which transfer electrons from suitable developer components (reducing agents) to atmospheric oxygen. Preference is given here to oxidases, such as tyrosinase, ascorbate oxidase and laccase, or else glucose oxidase, uricase or pyruvate oxidase. Mention may also be made of the procedure to intensify the action of small amounts (e.g. 1% and below, based on the overall composition) of hydrogen peroxide using peroxidases.

Expediently, the preparation of the oxidizing agent is then mixed directly prior to coloring the hair with the preparation containing the dye precursors. The ready-to-use hair-coloring preparation formed here should preferably have a pH in the range from 6 to 10. Particular preference is given to application of the hair colorant in a weakly alkaline medium. The application temperatures can be in a range between 15 and 40° C., preferably at the temperature of the scalp. After a contact time of about 5 to 45, in particular 15 to 30, minutes, the hair colorant is removed from the hair to be colored by rinsing out. Afterwashing with a shampoo is dispensed with if a strongly surfactant-containing carrier, e.g. a color shampoo, has been used.

Particularly in the case of hair which is difficult to color, the preparation containing the dye precursors can be applied to the hair without prior mixing with the oxidation component. Then, after a contact time of from 20 to 30 minutes—optionally after interim rinsing—the oxidation component is applied. After a further contact time of from 10 to 20 minutes, the hair is then rinsed and, if desired, after-shampooed. In this embodiment, according to a first variant in which the prior application of the dye precursors is thoughts to effect better penetration into the hair, the corresponding composition is adjusted to a pH of about 4 to 7. According to a second variant, an air oxidation is firstly attempted, where the applied composition preferably has a pH of from 7 to 10. In the case of subsequent accelerated post-oxidation, the use of peroxydisulfate solutions which have been made acidic as oxidizing agents may be preferred.

In addition, the development of the coloration can be supported and increased by adding certain metal ions to the composition. Such metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. Particularly suitable in this connection are $Zn^{2+}$, $Cu^{2+}$ and $Mn^{2+}$. The metal ions can in principle be used in the form of any desired physiologically compatible salt.

Preferred salts are the acetates, sulfates, halides, lactates and tartrates. By using these metal salts, it is possible both to accelerate the development of the coloration and also to influence the color nuance in a targeted manner.

The invention secondly provides compositions for improving the washfastness of colored fibers and for intensifying the coloration, in particular of keratin fibers, which comprise a combination of a sugar surfactant (A), a fatty acid partial glyceride (B) and a polymer.

With regard to further components of these compositions, reference is made to that stated above.

The invention thirdly provides for a method of improving the washfastness of colorations of fibers, in particular of keratin fibers, in which a coloring composition containing the active ingredient combination according to the invention, as used in any of claims 1 to 16, is applied to the fibers, where the composition is, if desired, rinsed out again after a contact time of from 1 to 45 minutes.

Finally, the invention fourthly provides a method of improving the washfastness of colorations of fibers, in particular of keratin fibers, in which, in a first step, a composition as used in any of claims 1 to 16 is applied to the fibers and then, in a second step, the fibers are colored in the usual manner. Within the scope of this method, it may be preferred to apply the first composition in the form of a spray.

EXAMPLES

Unless noted otherwise, all amounts are parts by weight.

1. Demonstration of Activity

The hair-coloring cream bases having the compositions listed in the table below were prepared. The constituents were mixed together in the order given. The oxidative development of the coloration was carried out in a mixing in the ratio 5:4 with 5% strength hydrogen peroxide dispersion. The contact time on the hair from Kerling, type "natural white", was 30 minutes at 25° C. When the coloring process was complete, the hair was rinsed and washed with an aqueous solution consisting of 1.0% by weight of Texapon® NSO, pH—6–7, and then dried. Each hair tress was measured at eight points using a color-measuring system from Datacolor. For this, the sample to be measured was fixed in a mounting device on a spectrophotometer, the reflectance values were measured over the range of visible light from 390–700 nm at intervals of 10 nm and the results were processed by means of a computer. The computer program determined the standard color values according to the CIE system in accordance with DIN 5033. The standard with regard to color intensity and washfastness used was the composition distinguished in each case by "C". For this, the color intensity of the washed tresses colored using these compositions was determined by colorimetry and set as 100%. The color intensities relative to this of the washed tresses colored using the other compositions are given in the table. The residual color strength of the hair tresses washed a further 6 times was determined relative to the hair tress washed once. These values are likewise given in the table.

| Composition/action | Brown 1 | Brown C1 | Copper 2 | Copper C2 | Garnet 3 | Garnet C3 |
|---|---|---|---|---|---|---|
| Lamesoft ® PO 65 (Cognis) Coco Glucosid (and) Glyceryl Oleate | 3.0 | — | 3.0 | — | 3.0 | — |
| Texapon ® NSO (Cognis, ca. 28%) Sodium Laureth Sulfate | 12.0 | 15.0 | 12.0 | 15.0 | 12.0 | 15.0 |
| Dehyton ® K (Cognis, ca. 30%) | 12.5 | 12.5 | 12.5 | 12.5 | 12.5 | 12.5 |
| Kokoslorol C12–18 (Cognis) | 2.0 | 2.0 | 2.0 | 2.0 | 2.0 | 2.0 |
| Hydrenol ® D (Cognis) | 8.5 | 8.5 | 8.5 | 8.5 | 8.5 | 8.5 |
| Eumulpin ® B2 (Cognis) | 0.75 | 0.75 | 0.75 | 0.75 | 0.75 | 0.75 |
| Ascorbic acid | 0.4 | 0.4 | 0.4 | 0.4 | 0.4 | 0.4 |
| Sodium sulfite | 0.4 | 0.4 | 0.4 | 0.4 | 0.4 | 0.4 |
| Arginine | — | — | — | — | 1.0 | 1.0 |
| Sodium silicate | — | — | 0.1 | 0.1 | — | — |
| Gluadin ® W40 (Cognis, ca. 40%) | 2.0 | 2.0 | — | — | — | — |
| Ammonia | ad pH 8–9 | ad pH 8–9 | ad pH 8–9 | ad pH 8–9 | ad pH 8–9 | ad pH 8–9 |
| p-Tolylenediamine sulfate | 0.6 | 0.6 | 0.2 | 0.2 | 0.13 | 0.13 |
| 2-Methylresorcinol | 0.3 | 0.3 | 0.08 | 0.08 | 0.7 | 0.7 |
| 4-Chlororesorcinol | 0.06 | 0.06 | 0.3 | 0.3 | — | — |
| Tetraaminopyrimidine sulfate | — | — | 0.36 | 0.36 | 1.2 | 1.2 |
| 3-Methyl-4-aminophenol | — | — | 0.44 | 0.44 | — | — |
| 2,7-Dihydroxynaphthalene | — | — | 0.3 | 0.3 | — | — |
| 2-Amino-6-chloro-4-nitrophenol | — | — | 0.1 | 0.1 | — | — |
| 1-(2'-Hydroxy-ethyl) amino-4-methyl-2-nitro-benzene | — | — | — | — | 0.05 | 0.05 |
| Water | | | ad 100 | | | |
| Color intensity in % | 115 | 100 | 111 | 100 | 107 | 100 |
| Residual color intensity in % | 89 | 83 | 92 | 62 | 99 | 93 |

2. Application Examples

2.1. Hair rinse

| | |
|---|---|
| Eumulgin ® B2[1] | 0.3 |
| Cetyl/stearyl alcohol | 3.3 |
| Isopropyl myristate | 0.5 |
| Lamesoft ® PO 65 | 0.5 |
| Dehyquart ® A-CA[2] | 2.0 |
| Salcare ® SC 96[3] | 1.0 |
| Citric acid | 0.4 |
| Gluadin ® WQ[4] | 2.0 |
| Phenonip ®[5] | 0.8 |
| Water | ad 100 |

[1]Cetylstearyl alcohol + 20 EO (INCI name: Ceteareth-20) (COGNIS)
[2]Trimethylhexadecylammonium chloride ca. 25% active substance (INCI name: Cetrimonium Chloride) (COGNIS)
[3]N,N,N-Trimethyl-2[(methyl-1-oxo-2-propenyl)oxy]-ethaneaminium chloride homopolymer (50% active substance; INCI name: Polyquaternium-37 (and) Propylene Glycol Dicaprylate Dicaprate (and) PPG-1 Trideceth-6) (ALLIED COLLOIDS)
[4]Cationized wheat protein hydrolyzate ca. 31% active substance (INCI name: Laurdimonium Hydroxypropyl Hydrolyzed Wheat Protein) (COGNIS)
[5]Hydroxybenzoic methyl ester-hydroxybenzoic ethyl ester-hydroxybenzoic propyl ester-hydroxybenzoic butyl ester-phenoxyethanol mixture (ca. 28% active substance; INCI name: Phenoxyethanol, Methylparaben, Ethylparaben, Propylparaben, Butylparaben) (NIPA)

2.2 Hair rinse

| | |
|---|---|
| Eumulgin ® B2 | 0.3 |
| Cetyl/stearyl alcohol | 3.3 |
| Isopropyl myristate | 0.5 |
| Paraffin oil perliquidum 15 cSt. DAB 9 | 0.3 |
| Dehyquart ® L 80[6] | 0.4 |
| Lamesoft ® PO 65 | 1.5 |
| Cosmedia Guar ® C 261[7] | 1.5 |
| Promois ® Milk-CAQ[8] | 3.0 |
| Citric acid | 0.4 |
| Phenonip ® | 0.8 |
| Water | ad 100 |

[6]Bis(cocoylethyl)hydroxyethylmethylammonium methosulfate (ca. 76% active substance in propylene glycol; INCI name: Dicocoylethyl Hydroxyethylmonium Methosulfate, Propylene Glycol) (COGNIS)
[7]Guar hydroxypropyltrimethylammonium chloride; INCI name: Guar Hydroxypropyl Trimonium Chloride (COGNIS)
[8]INCI name: Cocodimonium Hydroxypropyl Hydrolyzed Casein (SEIWA KASEI)

2.3. Hair treatment

| | |
|---|---|
| Dehyquart ® F75[9] | 4.0 |
| Cetyl/stearyl alcohol | 4.0 |
| Paraffin oil perliquidum 15 cSt. DAB 9 | 1.5 |
| Dehyquart ®A CA | 4.0 |
| Lamesoft ® PO 65 | 1.0 |
| Salcare ® SC 96 | 1.5 |
| Amisafe-LMA-60 ® 10 | 1.0 |
| Gluadin ® W 20[11] | 3.0 |
| Citric acid | 0.15 |
| Phenonip ® | 0.8 |
| Water | ad 100 |

[9]Fatty alcohols-methyltriethanolammonium methosulfate dialkyl ester mixture (INCI name: Distearoyl Hydroxyethylmonium Methosulfate, Cetearyl Alcohol) (COGNIS)
[10]INCO name Hydroxypropyl Arginine Lauryl/Myristyl Ether HCl (Ajinomoto)
[11]Wheat protein hydrolyzate (20% active substance in water; INCI name: Aqua (and) Hydrolyzed Wheat Protein (and) Sodium Benzoate (and) Phenoxyethanol (and) Methylparaben (and) Propylparaben) (COGNIS)

2.4. Hair treatment

| | |
|---|---|
| Dehyquart ® L80 | 2.0 |
| Cetyl/stearyl alcohol | 6.0 |
| Paraffin oil perliquidum 15 cSt. DAB 9 | 2.0 |
| Rewoquat ®W 75[12] | 2.0 |
| Cosmedia Guar ® C261 | 0.5 |
| Lamesoft ® PO 65 | 0.5 |
| Sepigel ® 305[13] | 3.5 |
| Honeyquat ® 50[14] | 1.0 |
| Gluadin ® WQ | 2.5 |
| Gluadin ® W 20 | 3.0 |
| Citric acid | 0.15 |
| Phenonip ® | 0.8 |
| Water | ad 100 |

[12]1-Methyl-2-nortallow-alkyl-3-tallow-fatty acid amidoethylimidazolinium methosulfate (ca. 75% active substance in propylene glycol; INCI name: Quaternium-27, Propylene Glycol) (WITCO)
[13]Copolymer of acrylamide and 2-acrylamido-2-methylpropanesulfonic acid (INCI name: Polyacrylamide (and) $C_{13}$–$C_{14}$ Isoparaffin (and) Laureth-7) (SEPPIC)
[14]INCI name: Hydroxypropyltrimonium Honey (BROOKS)

2.5. Hair treatment

| | |
|---|---|
| Dehyquart ® F75 | 0.3 |
| Salcare ® SC 96 | 5.0 |
| Gluadin ® WQ | 1.5 |
| Lamesoft ® PO 65 | 0.5 |
| Dow Corning ® 200 Fluid, 5 cSt.[15] | 1.5 |
| Gafquat ® 755N[16] | 1.5 |
| Biodocarb ®[17] | 0.02 |
| Perfume oil | 0.25 |
| Water | ad 100 |

[15]Polydimethylsiloxane (INCI name: Dimethicone) (DOW CORNING)
[16]Dimethylaminoethyl methacrylate-vinylpyrrolidone copolymer, quaternized with diethyl sulfate (19% active substance in water; INCI name: Polyquaternium-11) (GAF)
[17]3-Iodo-2-propynyl n-butylcarbamate (INCI name: Iodopropynyl Butylcarbamate) (MILKER & GRUNING)

2.6. Hair treatment

| | |
|---|---|
| Sepigel ® 305 | 5.0 |
| Dow Corning ® Q2-5220[18] | 1.5 |
| Promois ® Milk Q[19] | 3.0 |
| Lamesoft ® PO 65 | 0.5 |
| Polymer P1 corresponding to DE 3929173 | 0.6 |
| Genamin ® DSAC[20] | 0.3 |
| Phenonip ® | 0.8 |
| Perfume oil | 0.25 |
| Water | ad 100 |

[18]Silicone-glycol copolymer (INCI name: Dimethicone Copolyol) (DOW CORNING)
[19]INCI name Hydroxypropyltrimonium Hydrolyzed Casein ca. 30% active substance (SEIWA KASEI)
[20]Dimethyldistearylammonium chloride (INCI name: Distearyldimonium chloride) (CLARIANT)

2.7. Shampoo

| | |
|---|---|
| Texapon ® NSO[21] | 40.0 |
| Dehyton ® G[22] | 6.0 |

| 2.7. Shampoo | |
| --- | --- |
| Polymer JR 400 ®[23] | 0.5 |
| Cetiol ® HE[24] | 0.5 |
| Ajidew ® NL 50[25] | 1.0 |
| Lamesoft ® PO 65 | 3.0 |
| Gluadin ® WQT[26] | 2.5 |
| Gluadin ® W 20 | 0.5 |
| Panthenol (50%) | 0.3 |
| Vitamin E | 0.1 |
| Vitamin H | 0.1 |
| Citric acid | 0.5 |
| Sodium benzoate | 0.5 |
| Perfume | 0.4 |
| NaCl | 0.5 |
| Water | ad 100 |

[21]sodium lauryl ether sulfate ca. 28% active substance (INCI name: Sodium Laureth Sulfate) (COGNIS)
[22](INCI name: Sodium Cocoamphoacetate, ca. 30% active substance in water) (COGNIS)
[23]quaternized hydroxyethylcellulose (INCI name: Polyquaternium-10) (UNION CARBIDE)
[24]polyol fatty acid ester (INCI name: PEG-7 Glyceryl Cocoate) (COGNIS)
[25]sodium salt of 2-pyrrolidine-5-carboxylic acid (50% active substance: INCI name: Sodium PCA) (AJINOMOTO)
[26]INCI name: Hydroxypropyltrimonium Hydrolyzed Wheat Protein (COGNIS)

| 2.8. Shampoo | |
| --- | --- |
| Texapon ® NSO | 43.0 |
| Dehyton ® K[27] | 10.0 |
| Plantacare ® 1200 UP[28] | 4.0 |
| Lamesoft ® PO 65 | 2.5 |
| Euperlan ® PK 3000[29] | 1.6 |
| Arquad ® 316[30] | 0.8 |
| Polymer JR ® 400 | 0.3 |
| Gluadin ® WQ | 4.0 |
| Glucamate ® DOE 120[31] | 0.5 |
| Sodium chloride | 0.2 |
| Water | ad 100 |

[27]INCI name: Cocamidopropyl Betaine ca. 30% active substance (COGNIS)
[28]C12–C16 fatty alcohol glycoside ca. 50% active substance (INCI name: Lauryl Glucoside) (COGNIS)
[29]liquid dispersion of pearlescence-imparting substances and amphoteric surfactant (ca. 62% active substance; CTFA name: Glycol Distearate (and) Glycerin (and) Laureth-4 (and) Cocoamidopropyl Betaine) (COGNIS)
[30]tri-$C_{16}$-alkylmethylammonium chloride (AKZO)
[31]ethoxylated methyl glucoside dioleate (CTFA name: PEG-120 Methyl Glucose Dioleate) (AMERCHOL)

| 2.9. Shampoo | |
| --- | --- |
| Texapon ® N 70[32] | 21.0 |
| Plantacare ® 1200 UP | 8.0 |
| Lamesoft ® PO 65 | 3.0 |
| Gluadin ® WQ | 1.5 |
| Cutina ® EGMS[33] | 0.6 |
| Honeyquat ® 50[34] | 2.0 |
| Ajidew ® NL 50 | 2.8 |
| Antil ® 141[35] | 1.3 |
| Sodium chloride | 0.2 |
| Magnesium hydroxide | ad pH 4.5 |

| 2.9. Shampoo | |
| --- | --- |
| Water | ad 100 |

[32]sodium lauryl ether sulfate with 2 mol of EO ca. 70% active substance (INCI name: Sodium Laureth Sulfate) (COGNIS)
[33]ethylene glycol monostearate (ca. 25–35% monoester, 60–70% diester; INCI name: Glycol Stearate) (COGNIS)
[34]INCI name: Hydroxypropyltrimonium Honey (ca. 50% active substance) (BROOKS)
[35]polyoxyethylene-propylene glycol dioleate (40% active substance; INCI name: Propylene Glycol (and) PEG-55 Propylene Glycol Oleate) (GOLDSCHMIDT)

| 2.10. Shampoo | |
| --- | --- |
| Texapon ® K 14 S[36] | 50.0 |
| Dehyton ® K | 10.0 |
| Plantacare ® 818 UP[37] | 4.5 |
| Lamesoft ® PO 65 | 2.0 |
| Polymer P1, corresponding to DE 39 29 973 | 0.6 |
| Cutina ® AGS[38] | 2.0 |
| D-Panthenol | 0.5 |
| Glucose | 1.0 |
| Salicylic acid | 0.4 |
| Sodium chloride | 0.5 |
| Gluadin ® WQ | 2.0 |
| Water | ad 100 |

[36]sodium lauryl myristyl ether sulfate ca. 28% active substance (INCI name: Sodium Myreth Sulfate) (COGNIS)
[37]C8–C16 fatty alcohol glycoside ca. 50% active substance (INCI nmae: Coco Glucoside) (COGNIS)
[38]ethylene glycol stearate (ca. 5–15% monoester, 85–95% diester; INCI name: Glycol Distearate) (COGNIS)

| 2.11. Hair treatment | |
| --- | --- |
| Celquat ® L 200[39] | 0.6 |
| Luviskol ® K30[40] | 0.2 |
| D-Panthenol | 0.5 |
| Polymer P1, corresponding to DE 39 29 973 | 0.6 |
| Dehyquart ® A-CA[41] | 1.0 |
| Lamesoft ® PO 65 | 0.5 |
| Gluadin ® W 40[42] | 1.0 |
| Natrosol ® 250 HR[43] | 1.1 |
| Gluadin ® WQ | 2.0 |
| Water | ad 100 |

[39]quaternized cellulose derivative (95% active substance; CTFA name: Polyquaternium-4) (DELFT NATIONAL)
[40]polyvinylpyrrolidone (95% active substance; CTFA name: PVP) (BASF)
[41]cetyltrimethylammonium chloride (INCI name: Cetrimonium Chloride) (COGNIS)
[42]partial hydrolyzate from wheat ca. 40% active substance (INCI name: Hydrolyzed Wheat Gluten Hydrolyzed Wheat Protein) (COGNIS) [lacuna] ydroxyethylcellulose (AQUALON)

| 2.12. Color cream | |
| --- | --- |
| $C_{12-18}$-fatty alcohol | 1.2 |
| Lanette ® O[44] | 4.0 |
| Eumulgin ® B 2 | 0.8 |
| Cutina ® KD 16[45] | 2.0 |
| Lamesoft ® PO 65 | 4.0 |
| Sodium sulfite | 0.5 |
| L(+) - Ascorbic acid | 0.5 |

-continued

| 2.12. Color cream | |
|---|---|
| Ammonium sulfate | 0.5 |
| 1,2-Propylene glycol | 1.2 |
| Polymer JR ® 400 | 0.3 |
| p-Aminophenol | 0.35 |
| p-Tolylenediamine | 0.85 |
| 2-Methylresorcinol | 0.14 |
| 6-Methyl-m-aminophenol | 0.42 |
| Cetiol ® OE[46] | 0.5 |
| Honeyquat ® 50 | 1.0 |
| Ajidew ® NL 50 | 1.2 |
| Gluadin ® WQ | 1.0 |
| Ammonia | 1.5 |
| Water | ad 100 |

[44] cetylstearyl alcohol (INCI name: Cetearyl Alcohol) (COGNIS)
[45] self-emulsifying mixture of mono-/diglycerides of higher saturated fatty acids with potassium stearate (INCI name: Glyceryl Stearate SE) (COGNIS)
[46] di-n-octyl ether (INCI name: Dicaprylyl Ether (COGNIS)

| 2.13. Developer dispersion for color cream 2.12. | |
|---|---|
| Texapon ® NSO | 2.1 |
| Hydrogen peroxide (50% strength) | 12.0 |
| Turpinal ® SL[47] | 1.7 |
| Latekoll ® D[48] | 12.0 |
| Lamesoft ® PO 65 | 2.0 |
| Gluadin ® WQ | 0.3 |
| Salcare ® SC 96 | 1.0 |
| Water | ad 100 |

[47] 1-hydroxyethane-1,1-diphosphonic acid (60% active substance; INCI name: Etidronic Acid) (COGNIS)
[48] acrylic ester-methacrylic acid copolymer (25% active substance) (BASF)

The color cream had a pH of 10.0. It brought about an intensive red tinting of the hair.

| 2.14. Tinting shampoo | |
|---|---|
| Texapon ® N 70 | 14.0 |
| Dehyton ® K | 10.0 |
| Akypo ® RLM 45 NV[49] | 14.7 |
| Plantacare ® 1200 UP | 4.0 |
| Lamesoft ® PO 65 | 3.0 |
| Polymer P1, corresponding to DE 39 29 973 | 0.3 |
| Cremophor ® RH 40[50] | 0.8 |
| Dye C.I. 12 719 | 0.02 |
| Dye C.I. 12 251 | 0.02 |
| Dye C.I. 12 250 | 0.04 |
| Dye C.I. 56 059 | 0.03 |
| Preservative | 0.25 |
| Perfume oil | q.s. |
| Eutanol ® G[51] | 0.3 |
| Gluadin ® WQ | 1.0 |
| Honeyquat ® 50 | 1.0 |
| Salcare ® SC 96 | 0.5 |
| Water | ad 100 |

[49] lauryl alcohol + 4.5 ethylene oxide acetic acid sodium salt (20.4% active substance) (CHEM-Y)
[50] castor oil, hydrogenated + 45 ethylene oxide (INCI name: PEG-40 Hydrogenated Castor Oil) (BASF)
[51] 2-octyldodecanol (Guerbet alcohol) (INCI name: Octyldodecanol) (COGNIS)

Upon washing the hair with this tinting shampoo, the hair is given a lustrous, pale blonde shade.

| 2.15. Cream permanent wave | |
|---|---|
| Wave cream | |
| Plantacare ® 810 UP[52] | 5.0 |
| Thioglycolic acid | 8.0 |
| Turpinal ® SL | 0.5 |
| Ammonia (25% strength) | 7.3 |
| Ammonium carbonate | 3.0 |
| Cetyl/stearyl alcohol | 5.0 |
| Lamesoft ® PO 65 | 0.5 |
| Guerbet alcohol | 4.0 |
| Salcare ® SC 96 | 3.0 |
| Gluadin ® WQ | 2.0 |
| Perfume oil | q.s. |
| Water | ad 100 |
| Neutralizing solution | |
| Plantacare ® 810 UP | 5.0 |
| Hydrogenated castor oil | 2.0 |
| Lamesoft ® PO 65 | 1.0 |
| Potassium bromate | 3.5 |
| Nitrilotriacetic acid | 0.3 |
| Citric acid | 0.2 |
| Merquat ® 550[53] | 0.5 |
| Hydagen HCMF[54] | 0.5 |
| Gluadin ® WQ | 0.5 |
| Perfume oil | q.s. |
| Water | ad 100 |

[52] $C_8$–$C_{10}$-alkyl glucoside with degree of oligomerization of 1.6 (ca. 60% active substance) (COGNIS)
[53] dimethyldiallylammonium chloride-acrylamide copolymer (8% active substance; INCI name: Polyquaternium 7) (MOBIL OIL)
[54] chitosan powder (INCI name: Chitosan) (COGNIS)

What is claimed is:

1. A method of increasing the washfastness and color intensity of colored fibers which comprises applying to said fibers a composition comprising
   a) at least one sugar surfactant selected from the group consisting of alkyl and alkenyl oligoglycosides and fatty acid N-alkylpolyhydroxyalkylamides;
   b) at least one fatty acid partial glyceride of the Formula IV:

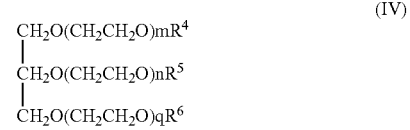

(IV)

wherein at least one of $R^4$, $R^5$, and $R^6$, is a $C_{6-22}$ acyl radical, at least one of $R^4$, $R^5$, and $R^6$ is H, and the remaining group is H or $C_{6-22}$ acyl radical, and the sum (m+n+q) is 0; and
   c) a surfactant.

2. The method of claim 1, wherein the composition additionally contains a polymer.

3. The method of claim 2, wherein the polymer is a cationic or amphoteric polymer.

4. The method of claim 3, wherein the cationic polymer is chosen from a) homopolymers of the general formula (V),

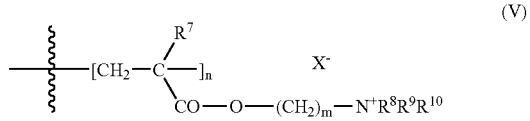

(V)

wherein $R^7$=—H or —$CH_3$; $R^8$, $R^9$ and $R^{10}$, independently of one another, are selected from the group consisting of $C_{1-4}$-alkyl, alkenyl and hydroxyalkyl groups; m=1, 2, 3 or 4; n is a natural number and $X^-$ is a physiologically compatible organic or inorganic anion, and b) copolymers consisting essentially of the monomer units listed in formula (V) and nonionogenic monomer units.

5. The method of claim 4 wherein $R^7$ is —$CH_3$; $R^8$, $R^9$ and $R^{10}$ are —$CH_3$ and m=2.

6. The method of claim 3, wherein the cationic polymers are chosen from the group consisting of
cationized cellulose derivatives,
cationized guar derivatives,
cationized honey and
cationic alkyl polyglycosides.

7. The method of claim 2, wherein the polymer is an anionic polymer.

8. The method of claim 7, wherein the anionic polymer has carboxylate and/or sulphonate groups.

9. The method of claim 8, wherein the anionic polymer is formed from the monomer 2-acrylamido-2-methylpropanesulfonic acid, where the sulfonic acid group may completely or partially be in the form of the sodium, potassium, ammonium, mono- or triethanolamine salt.

10. The method of claim 7, wherein the anionic polymer is a copolymer of at least one anionic monomer and at least one nonionogenic monomer.

11. The method of claim 10, wherein the anionic polymer is a copolymer consisting of 70 to 55 mol % of acrylamide and 30 to 45 mol % of 2-acrylamido-2-methylpropanesulfonic acid, wherein the sulfonic acid group is completely or partially present as a sodium, potassium, ammonium, mono- or triethanolammonium salt.

12. The method of claim 11, where the composition further contains a protein hydrolyzate or a derivative of a protein hydrolyzate.

13. The method of claim 12, wherein the protein hydrolyzate or derivative of the protein hydrolyzate is of vegetable origin.

14. The method of claim 1, wherein the surfactant is selected from the group consisting of anionic, zwitterionic, amphoteric and nonionic surfactants.

15. The method of claim 1, wherein the composition further contains a vitamin, a provitamin, a vitamin precursor or a derivative thereof.

16. The method of claim 1, wherein the composition further contains a plant extract.

17. A method of increasing the washfastness and color intensity of colored fibers, comprising:
applying a composition comprising at least one sugar surfactant selected from the group consisting of alkyl and alkenyl oligoglycosides and fatty acid N-alkylpolyhydroxyalkylamides and at least one fatty acid partial glyceride to said fibers; and
allowing the composition to remain on the fibers for longer than one hour.

18. The method of claim 17 wherein the fibers are keratin fibers.

19. The method of claim 17 wherein the fibers are hair.

20. A method of increasing the washfastness and color intensity of colored fibers, comprising:
applying to said fibers a composition comprising
at least one alkyl oligoglycoside, alkenyl oligoglycoside, or fatty acid N-alkylpolyhydroxyalkylamide; and
oleic acid monoglyceride.

* * * * *

UNITED STATES PATENT AND TRADEMARK OFFICE
CERTIFICATE OF CORRECTION

PATENT NO. : 7,169,193 B2  Page 1 of 1
APPLICATION NO. : 10/281578
DATED : January 30, 2007
INVENTOR(S) : Astrid Kleen et al.

It is certified that error appears in the above-identified patent and that said Letters Patent is hereby corrected as shown below:

Title Page,
Item (30) Foreign Application Priority Data:
Delete "100 20 887" and insert -- 100 20 887.8 --.

Title Page,
Item (56) References Cited, FOREIGN PATENT DOCUMENTS:
Delete "DE 0 561 825 B1 9/1995" and insert -- EP 0 561 825 B1 9/1995 --.

Signed and Sealed this

Fifth Day of February, 2008

JON W. DUDAS
*Director of the United States Patent and Trademark Office*